United States Patent [19]
Dalemans et al.

[11] Patent Number: 6,136,594
[45] Date of Patent: *Oct. 24, 2000

[54] REPLICATION DEFICIENT RECOMBINANT ADENOVIRUS VECTOR

[75] Inventors: Wilfried Dalemans, Heverlee-Egenhoven, Belgium; Michel Perricaudet; Leslie Stratford-Perricaudet, both of Ouarville, France; Andrea Pavirani, Strasbourg, France

[73] Assignee: Transgene S.A., Strasbourg, France

[*] Notice: This patent is subject to a terminal disclaimer.

[21] Appl. No.: 08/442,262

[22] Filed: May 16, 1995

Related U.S. Application Data

[63] Continuation of application No. 07/889,913, May 29, 1992, abandoned, which is a continuation of application No. 07/769,623, Oct. 2, 1991, abandoned.

[51] Int. Cl.[7] .......................... C12N 15/86; A01N 63/00
[52] U.S. Cl. .................. 435/320.1; 424/93.1; 424/93.2
[58] Field of Search ........................ 514/44; 435/320.1; 424/93.1, 204.1, 199.1, 233.1

[56] References Cited

U.S. PATENT DOCUMENTS

| | | | |
|---|---|---|---|
| 4,920,209 | 4/1990 | Davis et al. | 435/235 |
| 5,240,846 | 8/1993 | Collins et al. | 435/240.1 |

FOREIGN PATENT DOCUMENTS

WO 91/02796  3/1991  WIPO.

OTHER PUBLICATIONS

Boucher, 1996, "Current Status of CF Gene Therapy", TIG 12:81–84.

Brody et al., 1994, "Acute Responses of Non–Human Primates to Airway Delivery of an Adenovirus Vector Containing the Human Cystic Fibrosis Transmembrane Conductance Regulator cDNA", Hum. Gene Ther. 5:821–836.

Collins, 1992, "Cystic Fibrosis: Molecular Biology and Therapeutic Implications", Science 256:774–779.

Rosenfeld et al., 1992, "In Vivo Transfer of the Human Cystic Fibrosis Transmembrane Conductance Regulator Gene to the Airway Epithelium", Cell 68:143–155.

Chengalvalva et al., 1991, "Adenovirus Vectors for Gene Expression", Curr. Biol. 2:718–722.

(List continued on next page.)

*Primary Examiner*—Jasemine C. Chambers
*Assistant Examiner*—Deborah J. R. Clark
*Attorney, Agent, or Firm*—Pennie & Edmonds LLP

[57] ABSTRACT

The present invention relates to a replication deficient recombinant adenovirus vector in the genome of which is inserted an expression cassette comprising the DNA fragment coding for the human CFTR protein, said DNA fragment being placed under the control of the elements for the expression thereof.

The present invention also concerns a vector according to claim 1 wherein in the expression cassette the human CFTR gene is under the control of the endogenous human CFTR promoter.

15 Claims, 13 Drawing Sheets

OTHER PUBLICATIONS

Levrero et al., 1991, "Defective and Nondefective Adenovirus for Expressing Foreign Genes In Vitro and In Vivo", Gene 101:195–202.

Rosenfeld, 1991, "Adenovirus–Mediated Transfer of a Recombinant $\alpha_1$–Antitrypsin Gene to the Lung Epithelium in Vivo", Science 252:431–433.

Crystal et al., 1990, New Viral Transfer Systems, Abstract Presented at the North American Cystic Fibrosis Conference, Arlington, Virginia, Oct. 3–6.

Drumm et al., 1990, "Correction of the Cystic Fibrosis Defect In Vitro by Retrovirus by Retrovirus–Mediated Gene Transfer", Cell 62:1227–1233.

Gilardi et al., 1990, "Expression of Human $\alpha_1$–Antitrypsin Using a Recombinant Adenovirus Vector", FEBS 267:60–62.

Stratford–Petricaudet et al., 1990, "Evaluation of the Transfer and Expression in Mice of an Enzyme–Encoding Gene Using a Human Adenovirus Vector", Hum. Gene Ther. 1:241–256.

Chasse et al., 1989, "L'Adenovirus: Vecteur de Therapie Genique?", Medecine/Sciences 5:331–337.

Chasse et al., 1989, "Human Recombinant Adenovirus Used to Correct a Mouse Enzyme Deficiency", Abstract Presented at the Meeting on Regulation of Gene Expression, Cold Spring Harbor, May 3–7.

Chasse et al., 1989, "Somatic Gene Therapy of a Mouse Enzyme Deficiency Using a Recombinant Adenovirus", J. Cell. Biochem. S13B:174 (Abstract F120).

Ginsberg et al., 1989, "Role of Early Region 3 (E3) in Pathogenesis of Adenovirus Disease", Proc. Natl. Acad. Sci. USA 86:3823–3827.

Hubbard et al., 1989, "Fate of Aerosolized Recombinant DNA–Produced $\alpha_1$–Antitrypsin: Use of the Epithelial Surface of the Lower Respiratory Tract to administer Proteins of Therapeutic Importance", Proc. Natl. Acad. USA 86:680–684.

Riordan et al., 1989 "Identification of the Cystic Fibrosis Gene: Cloning and Characterization of Complementary DNA", Science 245:1066–1072.

Ballay et al., 1987, "Hepatitis B Adenovirus Recombinants as a Potential Live Vaccine", *Hepadna Viruses* (Alan R. Liss, Inc.) pp. 481–493.

Ballay et al., 1985, "In Vitro and In Vivo Synthesis of the Hepatitis B Virus Surface Antigen and of the Receptor for Polarized Human and Serum Albumin from Recombinant Human Adenoviruses", EMBO J. 4:3861–3865.

Long et al., 1984, "Complete Sequence of the cDNA for Human $\alpha_1$Antitrypsin and the Gene for the S Variant", Biochem. 23:4828–4837.

Shenk and Williams, 1984, "Genetic Analysis of Adenoviruses", Current Topics in Microbiology and Immunology 111:1–39.

Hanahan, 1983, "Studies and Transformation of *Escherichia coli* with Plasmids", J. Mol. Biol. 166:557–580.

Thimmappaya et al., 1982, "Adenovirus VAI RNA Is Required for Efficient Translation of Viral mRNAs at Late Times after Infection", Cell 31:543–551.

Kapoor and Chinnadurai, 1981, "Method for Introducing Site–Specific Mutations into Adenovirus 2 Genome: Construction of a Small Deletion Mutant in VA–$RNA_1$ Gene", Proc. Natl. Acad. Sci. USA 78:2184–2188.

Graham et al., 1977, "Characteristics of a Human Cell Line Transformed by DNA from Human Adenovirus Type 5", J. Virol. 36:59–72.

REPLICATION DEFICIENT RECOMBINANT ADENOVIRUS VECTOR

This application is a continuation application of U.S. Ser. No. 07/889,913, abandoned filed on May 29, 1992 which is a continuation application of U.S. Ser. No. 07/769,623, abandoned filed on Oct. 2, 1991.

FIELD OF INVENTION

The present invention relates to a replication deficient recombinant adenovirus vector and to a method of treatment of respiratory manifestations of cystic fibrosis (CF) by somatic gene therapy in using the said vector.

BACKGROUND OF THE INVENTION

The clinical manifestations of cystic fibrosis (CF), a common lethal hereditary disorder, are dominated by abnormalities of the airway epithelial surface, including chronic mucus production, infection, and inflammation (Boat et al., 1989). The gene responsible for CF, termed the "cystic fibrosis transmembrane conductance regulator" (CFTR) gene, is localized on chromosome 7 at q32 (Rommens et al., 1989; Riordan et al., 1989). The predicted CFTR protein is a 1480 residue single chain glycosylated molecule with twelve transmembrane domains and three intra-cytoplasmic domains containing sequences that can be phosphorylated by protein kinases (Riordan et al., 1989; Gregory et al., 1990). In vitro studies suggest that the CFTR protein is a Cl$^-$ channel that modulates the secretion of Cl$^-$ across the apical membrane of epithelial cells in response to elevations of intracellular cAMP (Anderson et al., 1991; Kartner et al., 1991). Mutations of the CFTR gene render epithelial cells unable to modulate Cl$^-$ secretion through the CFTR gene pathway (Frizzell et al., 1986; Li et al., 1988; Hwang et al., 1989). Importantly, in vitro studies have shown that transfer of the normal CFTR cDNA to epithelial cell lines derived from individuals with CF can override this abnormality, and permit the cells to secrete Cl$^-$ in response to increased intracellullar cAMP (Drumm et al., 1990; Rich et al., 1990).

These in vitro studies, and the knowledge that the lethal consequences of mutations of the gene occur almost exclusively in the lung (Boat et al, 1989), suggest the feasibility of somatic gene therapy for CF, i.e., it may be possible to correct the pulmonary manifestations caused by mutations of the CFTR gene by directly transferring a normal CFTR cDNA to airway epithelial cells in vivo. The major obstacles to this approach lie in the geometry of the lung and the biology of the airway epithelium. jthe epithelial cells of the human airway comprise an approximately 1–2 m$^2$ surface distributed over a successively branching "fractal-like" tree structure (Weibel, 1991), a geometry that makes it essentially impossible to treat CF successfully by removing the epithelial cells for in vitro correction and subsequent reimplantation. Further, the majority of the airway epithelial cells are terminally differentiated and those that are capable of proliferating do so at a slow rate (Evans and Shami, 1989).

SUMMARY OF THE INVENTION

Somatic gene therapy for the respiratory manifestations of CF requires a methodology capable of transferring the normal cDNA into non-proliferating airway epithelial cells, and this has to be done in vivo.

The solution according to the invention is to utilize a replication deficient recombinant adenovirus that contains an active promoter and a normal recombinant CFTR gene for the in vivo transfer of the human CFTR gene to the respiratory epithelium of the lungs (Graham, 1986; Berkner, 1988; Horowitz, 1990).

In this purpose, the present invention provides a replication deficient recombinant adenovirus vector in the genome of which is inserted an expression cassette comprising the DNA fragment coding for the human CFTR protein, said DNA fragment being placed under the control of the elements for the expression thereof. The elements for the expression of a gene are mainly a promoter; a translation start codon and a translation stop codon and eventually a terminator, as is well known in the Art.

Appropriately, the expression cassette comprises normal human CFTR cDNA.

Advantageously, the human CFTR cDNA is as naturally found especially without silent mutation in the region of the known CFTR cryptic promoter.

In one embodiment of the present invention, the vector is constructed from the adenovirus of type 5 (Ad 5). However, other types of adenovirus are as well appropriate which induce benign infections in human such as Ad2.

The safety of the viral vector system of the present invention is an important consideration. In this regard, the Ad-CFTR recombinant adenoviral vector may be constructed to be replication deficient by removal the majority of E1a and E1b, especially the complete E1a structure gene and part of the E1b structural gene.

The expression cassette may then be advantageously inserted in the place of the $E_1$ region of Ad5 after partial deletion thereof. The E1 region is essential for the replication of the virus and deletions therein render the virus less offensive.

Thus, while adenovirus is tropic for human respiratory epithelial cells and Ad-CFTR can readily infect human respiratory epithelial cells (Straus, 1984; Rosenfeld et al., 1991b), once inside the cell, the vector cannot replicate by itself. This cell inability to replicate limits the recombinant adenoviral infection to those epithelial cells infected initially, in contrast to that of wild type adenovirus which is capable of self-replication and infection of surrounding cells. Further, by rendering Ad-CFTR replication deficient, the most important negative consequence of adenoviral infection (cell lysis) is eliminated and the biosynthetic nyachinery of the host cells cannot be dominated by viral replication as is the case with a replication competent virus.

In the vector according to the present invention, the newly introduced CFTR gene may have the potential to be regulated or constitutive expression may be sufficient. The structural features of the CFTR gene promoter place it in the housekeeping class, implying that its expression may be constitutive (Yoshimura et al., 1991). However, the presence of multiple potential binding sites for known transcriptional regulatory factors suggest that it may also be regulatable and modulation of CFTR gene expression has been demonstrated in vitro (Yoshimura et al., 1991; Trapnell et al., 1991a). As a consequence, in a particular embodiment of the vector, a constitutive promoter may be used, such, as the Ad2 major late promoter. However, if regulation of Ad-CFTR directed CFTR expression is sought, a vector with the endogenous CFTR promoter optionally mutated may be used.

More particularly, the CFTR expression cassette may comprise a vector according to claim 1 wherein the CFTR expression cassette comprises successively from 5' to 3'

1) the ITR, the origin of replication, the encapsidation signal and the E1a enhancer of Ad5;

2) the major late promoter, and the Tripartite leader sequence of Ad2;

3) the DNA fragment coding for human CFTR, and 4) the SV40 polyadenylation addition signal.

The encapsidation signal may be mutated so as to decrease its encapsidation power.

The Tripartite leader sequence of Ad2 enhances the translation but may be omitted.

The regions, which are not essential for the survival of the adenovirus such as $E_3$, may also be deleted to insert the expression cassette.

The present invention demonstrates that it is possible to use an adenoviral vector of the present invention to transfer a recombinant normal CFTR cDNA to the lung where it is expressed for at least 6 wk.

Indeed, the present invention provides a method for the treatment by gene therapy for the pulmonary and respiratory manifestations of cystic fibrosis comprising the in vivo administration in the respiratory epithelium of a replication deficient recombinant adenovirus vector whose genome is inserted an expression cassette comprising the DNA fragment coding for the human CFTR protein, said DNA fragment being placed under the control of the elements for the expression thereof.

Particularly, the present invention provides a method comprising intratracheal administration of a replication deficient recombinant adenovirus vector in the genome of which is inserted an expression cassette comprising the DNA fragment coding for the human CFTR protein, said DNA fragment being placed under the control of the elements for the expression thereof as above specified.

The present invention also provides pharmaceutical compositions for the treatment of the pulmonary and respiratory manifestations of cistic fibrosis comprising, as active ingredient, a replication deficient recombinant adenovirus vector in the genome of which is inserted an expression cassette comprising the DNA fragment coding for the human CFTR protein, said DNA fragment being placed under the control of the elements for the expression thereof as above specified, and a vehicle appropriate for intratracheal administration especially inhalation thereof.

The approach of the invention is particularly efficient and advantageous based on the following facts: (1) the lethal manifestations of CF involve the respiratory epithelium (Boat et al., 1989); (2) the CFTR gene is expressed in airway epithelial cells (Jefferson et al., 1991b); (3) the respiratory manifestations of CF do not recur following transplantation of a normal lung into a CF individual (de leval et al., 1991); (4) the defective cAMP-mediated $Cl^-$ secretion in epithelial cells derived from individuals with CF can be restored by transfer of a normal human CFTR cDNA into the cells (Drumm et al., 1990); (5) the complex anatomy of the human airway epithelial surface precludes the approach to gene therapy of removing defective cells for in vitro gene transfert of a normal gene and reimplantation of these cells (Weibel, 1991); and (6) the slow rate of respiratory tract epithelial cell turnover favors a vector (such as adenovirus) that does not require host cell proliferation for recombinant gene expression (Berkner, 1988; Evans and Shami, 1989).

Several observations in the present invention show that this approach is feasible. Following in vivo respiratory tract infection with Ad-CFTR, in situ analysis demonstrated Ad-CFTR derived human CFTR mRNA expression in the respiratory epithelium, which is the site of the CF epithelial cell $Cl^-$ secretory defect and where the normal CFTR gene is expressed (Knowles et al., 1981; Knowles et al., 1983; Frizzell et al., 1986; Jetton et al, 1989; Li et al., 1988; Boat et al., 1989; Hwang et al., 1989; Rich et al, 1990; Zeitlin et al, 1991; Yoshimura et al., 1991 Chu et al., 1991; Trapnell et al., 1991b). Further, human CFTR mRNA transcripts were etected in cotton rat lungs for 6 wk. Finally, in vitro studies demonstrated that Ad-CFTR was capable of directing the synthesis on intact, functional CFTR protein. In this regard, in 293 human embryonic kidney cells (cells that normally do not express detectable CFTR mRNA transcripts by northern nor demonstrate cAMP-mediated $Cl^-$ secretion as evidenced by $^{36}Cl^-$ efflux studies) and in CFPAC-1 cells [a human pancratic epithelial cell line derived from a deltaF508 CF homozygote which expresses the "CF phenotype", i.e., does not secrete $Cl^-$ in response to cAMP (Schoumacher et al., 1990)], infection with Ad-CFTR resulted in de novo biosynthesis of CFTR molecules and conveyed to these cells the ability to increase $Cl^-$ secretion in response to elevations in cAMP.

Gene therapy for CF may require only low level expression of the normal CFTR to correct the defective physiology in the airway epithelium necessary to reverse the disease process. It is known that individuals heterozygous for the normal and common abnormal deltaF508 CFTR alleles are clinically well and express both alleles in the respiratory epithelium equally at the mRNA levels (Trapnell et al., 1991b). Quantitative studies show that CFTR mRNA is expressed in low abundance at about 1–2 copies/cell on average in the human airway epithelium and indirect evidence suggests that the CFTR gene is likely expressed in the ciliated cell, the predominant cell type found in this epithelium (Trapnell et al., 1991b). Consistent with this feature, complementation studies in which the normal CFTR cDNA has been transferred with a retrovirus in vitro to correct the abnormal $CFCl^-$ secretory phenotype in epithelial cells derived from an individual with CF show that low level expression of the normal CFTR gene is sufficient (Drumm et al., 1990). Consequently, the observation that Ad-CFTR-directed human CFTR mRNA transcripts can be detected by northern, PCR and in situ analysis in cotton rat lung after Ad-CFTR infection in vivo and that human CFTR protein can be detected in airway epithelial cells recovered from these animals provide evidence that this approach can provide adequate expression to complement the abnormal CFTR gene expression in respiratory epithelium of CF individuals. In regard to delivery to specific cell types, the in situ hybridization analysis of the Ad-CFTR infected animals shows that Ad-CFTR expression in the airway epithelium is extensive, consistent with the likely widespread expression of defective $Cl^-$ in CF.

Moreover, the adenovirus has advantages as a vector system in gene therapy of CF with regard to respiratory epithelial tropism, ease of producing high titer recombinant virus, high infectivity rate and no dependence on target cell proliferation.

Finally, unexpectedly the overexpression of CFTR Protein doesn't induce a lethal toxicity.

DETAILED DESCRIPTION

The detailed description which follows is designed to illustrate other features and advantages of the present invention.

To evaluate the feasibility of direct transfer of the normal cystic fibrosis transmembrane conductance regulator (CFTR) gene to the airway epithelium as an approach to gene therapy for the respiratory manifestations of cystic fibrosis (CF), a replication deficient recombinant adenovirus (Ad) vector (Ad-CFTR) including the Ad 2 major late promoter and normal human CFTR cDNA was introduced into the trachea of cotton rats. Two days after infection with Ad-CFTR, in situ analysis of rat lung tissue demonstrated human CFTR gene expression in the respiratory epithelium and evaluation of lung RNA by northern analysis revealed intact human CFTR mRNA transcripts. Polymerase chain reaction amplification of reverse transcribed lung RNA using primers specific for human CFTR m.RNA transcribed from Ad-CFTR infection. In vitro studies using the CFPAC-1 CF epithelial cell line demonstrated that Ad-CFTR infection directed the expression of a functional human CFTR protein as evidenced by protein of the exprected size and correction of the defect in cAMP-mediated Cl⁻ secretion of these cells. Human CFTR protein was detected in epithelial cells using anti-human CFTR antibody 11–14 days after infection. Direct transfer and expression of the normal CFTR gene in vivo holds promise for treatment of the pulmonary manifestations of CF.

Panels B–C. Evaluation of forskolin stimulated Cl⁻ efflux in the 293 human embryonic kidney cells before and after infection with Ad-CFTR. B. Uninfected 293 cells. C. 293 cells infected with Ad-CFTR. Panels D–E. Ad-CFTR correction of the Cl⁻ efflux defect in epithelial cells derived from an individual homozygous for the deltaF508 mutation. Panel D. Uninfected CFPAC-1 cells. Panel E. CFPAC-1 cells infected with Ad-alpha1AT, as a negative control. Panel F. CFPAC-1 cells infected with Ad-CFTR.

FIGS. 6A–L represent the immunohistochemical localization of human CFTR after in vivo infection of cotton rat lung with Ad-CFTR. Shown are cytocentrifuge preparations of various controls nd of cells obtained by cytologic brush from cotton rat respiratory tract obtained 11–14 days after Ad-CFTR intracheal instillation. Immunoreactivity to human CFTR using a primary mouse anti-human CFTR monoclonal antibody is indicated by a red color, and cell nuclei appear blue as a result of hematoxylin counterstaining. (A) Control T84 colon epithelial cells (×1000). (B) Cotton rat airway epithelial cells, uninfected (×1000). (C) Same as (B), but infected in vitro with Ad-CFTR (×1000). (D) Cotton rat airway epithelial cells from an uninfected animal, 14 days after instillation of the virus dialysis Buffer (×830?). (E) Similar to (D), 11 days after receiving ??? (×1000). (F) Cotton rat airway epithelial cells from an animal 11 days after infection with the control virus Ad-d1312 (×1000). (G) Cotton rat airway epithelial cells from an animal 14 days after infection with Ad-CFTR (×630?). (H and I) Similar to (G). Other examples (all ×1000). (J) Similar to (G), 11 days after infection with Ad-CFTR (×1000). (K) Similar to (J) (×1600). (L) Similar to (J), but with the primary anti-CFTR antibody omitted (×1000).

EXAMPLE 1

Construction of a Recombinant Adenoviral Vector Ad-CFTR

Figure 1:
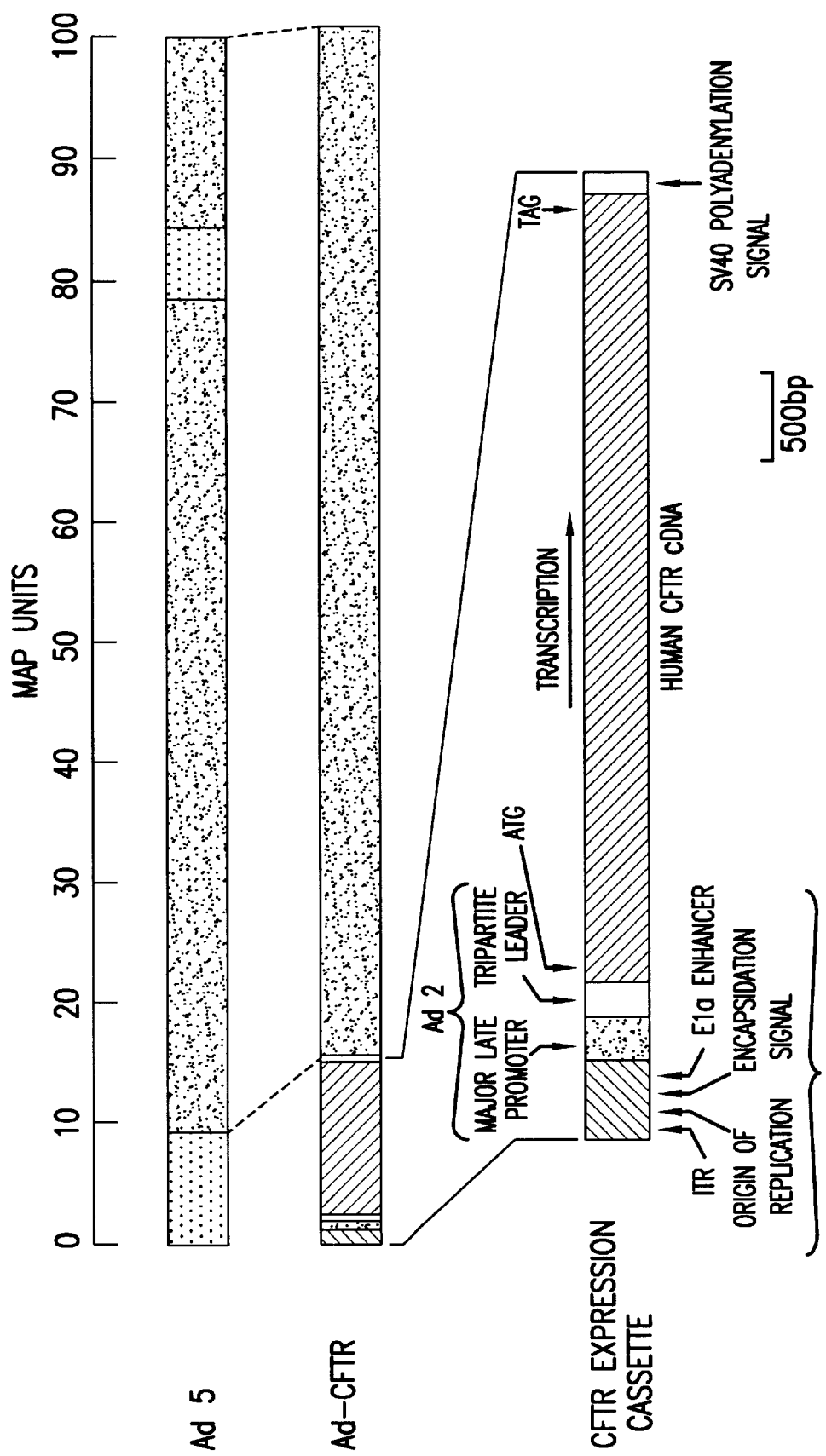
In FIG. 1 is schematically represented the recombinant adenoviral vector Ad-CFTR of example 1. Shown are the adenovirus type 5 (Ad 5) genome, the recombinant adenoviral DNA containing the human CFTR cDNA (Ad-CFTR) and a detailed enlargement of the CFTR expression cassette. Ad 5 DNA is divided into 100 map units (mu) [360 base pairs (bp)/mu]. Stippled segments of Ad 5 indicate deletions of the majority of the E1 region (0–9.2 mu) and E3 (78.4–84.3 mu) which were removed in the construction of Ad-CFTR to allow room for insertion of exogenous, nonviral DNA. The CFTR expression cassette includes: the 5' inverted terminal repeat (ITR), origin of replication, encapsidation signal, and E1a enhancer (all from Ad 5); the major late promoter and a copy of the tripartite leader sequence cDNA [from nucleotide 123 to 4587 (see Riordan et al., for sequence numbering)]; and the SV40 early mRNA polyadenylation signal. The CFTR protein translation start (ATG) and stop (TAG) signals are indicated.
Figure 2A:
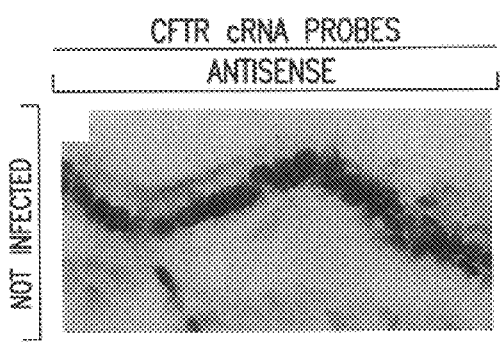
FIGS. 2A–H represents the evaluation of Ad-CFTR-directed human CFTR mRNA transcripts in lungs of cotton rats by in situ hybridization analysis reported in example 2. Shown are sections through bronchial epithelium from an uninfected animal and an animal two d after infection with Ad-CFTR evaluated with antisense CFTR cRNA probes (Panels A, C, E, G) and control, sense CFTR probes (Panels B, D, F, H). Panels A, B. Uninfected cotton rat. Panels C–H. Cotton rat infected with Ad-CFTR.
Figure 2B:
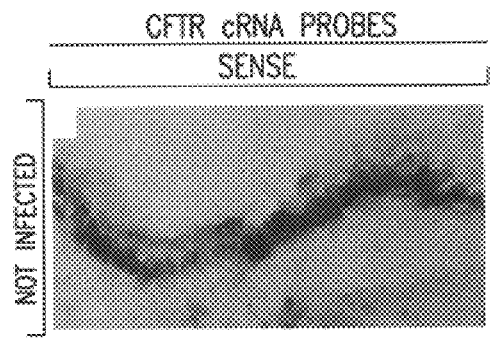
Figure 2C:
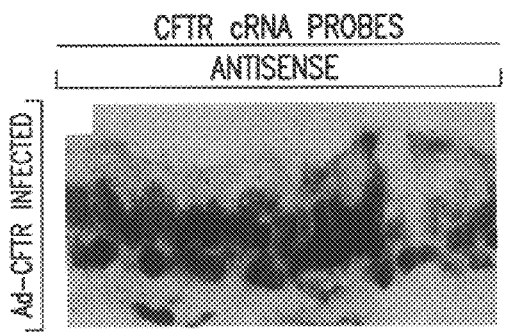
Figure 2D:
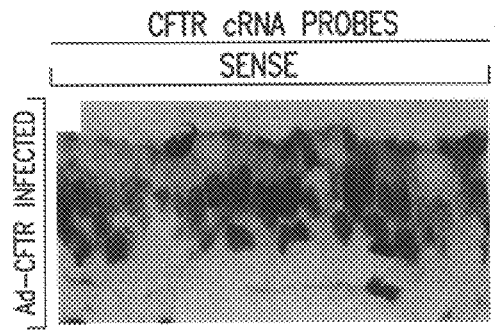
Figure 2E:
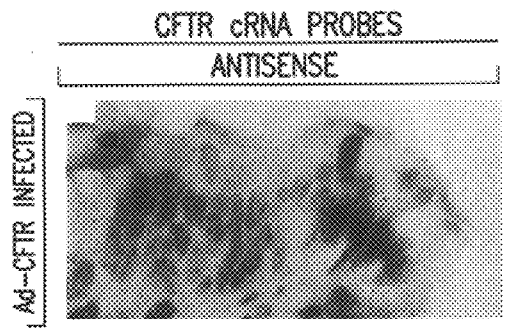
Figure 2F:
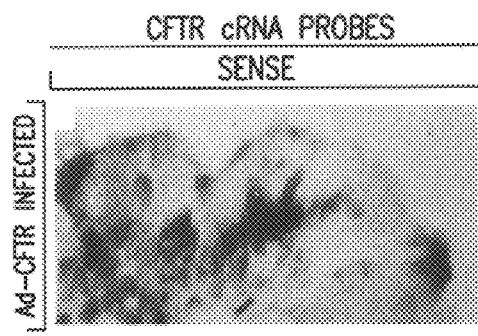
Figure 2G:
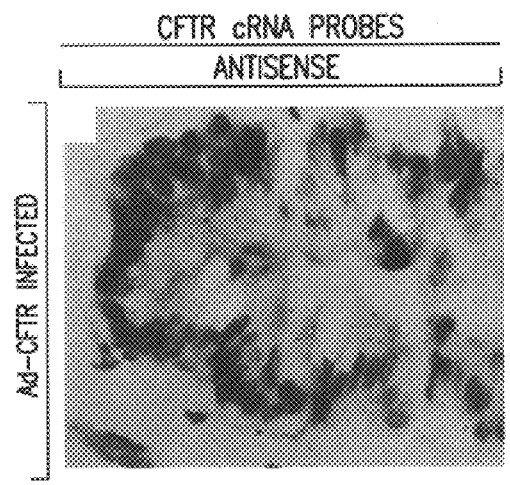
Figure 2H:
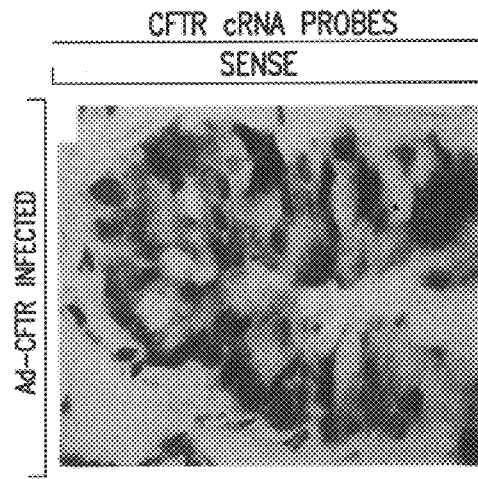

Ad-CFTR, a replication-deficient recombinant adenovirus containing the human CFTR protein coding sequence cDNA, was constructed using a modified type 5 adenoviral (Ad 5) genome (FIG. 1). The majority of the E3 region [78.4 to 84.3 map units (mu)] was deleted to provide space for insertion of a cassette containing the 4.5 kb coding sequence of the human CFTR gene (Thimmappaya et al., 1982); (Riordan et al., 1989). The left end of the viral genome [0 to 9.2 mu (the majority of the E1a and E1b regions)] was deleted and replaced by the CFTR expression cassette which contained essential viral cis-acting elements including the inverted terminal repeat (ITR), origin of replication, and the encapsidation signal, as well as the E1a enhancer, but not the E1a structural gene, a substitution that eliminates autonomous replication of the recombinant vector by removal of the E1a function. The E1a enhancer was followed by the Ad 2 major late promoter, the Ad2 tripartite leader, and a 4.5 kb CFTR CDNA [nucleotides 1 23–4587 (see Riordan et al., 1989 for sequence numbering)].

Within the Ad-CFTR expression cassette, the adenoviral type 2 (Ad 2) major late promoter (MLP) was used to drive transcription of human CFTR mRNA sequences. The majority of the Ad 2 tripartite leader sequence cDNA was included to increase the translation efficiency of CFTR protein expression (Mansour et al., 1986).

More specifically, the recombinant adenovirus Ad-CFTR was constructed from the adenovirus-type 5 (Ad 5) deletion mutant, Ad-d1324 (Thimmappaya et al., 1982) and a plasmid (pTG5955) containing the 5' inverted terminal repeat, origin of replication, encapsidation signal, and E1a enhancer (all from Ad 5); the major late promoter and the majority of the tripartite leader sequence cDNA (both from Ad 2); the 4.5 kb human CFTR cDNA including the entire protein coding sequence; the SV40 early polyadenylation signal; and the Ad 5 sequences from nucleotide positions 3329 to 6241.

pTG5955 was constructed as follows: A restriction site SmaI was introduced into the HindIII site of pMLP10 (Levrero M. et al. (1991) (48), generating pMLP11. In this plasmid, the left ITR of Ad5 is combined with the major late promoter and the three viral leader sequences of Ad2. This provides the signals for replication and encapsidation, as well as the gene expression signals. (For more details, refer to the publications of Levrero et al., 1991, and Gilardi et al., 1990 (49).

In the Sma site of pMLP11, the following DNA fragments were introduced (5' to 3'):

the CFTR cDNA from nucleotide positions 123 to 4587; the amino acid composition corresponds to the sequence published by Riordan J. R. et al. (1989) (32), with the exception of a Met to Val change at amino acid residue 470;

the SV40 poly(A) site (nucleotides 2533–2666);

the Ad5 nucleotide sequences from 3329 to 6241.

The total CFTR-cDNA insert was sequenced on both strands, confirming the amino acid composition of the corresponding CFTR protein.

Plasmid pTG 5955 was linearized by ClaI cleavage and cotransfected with ClaI-cut-Ad-d1324 DNA into 293 cells to allow homologous recombination to occur. Recombinant adenoviral DNA was replicated and encapsidated into infectious virions which were screened after by plaque purification. Individual plaques were amplified in 293 cells (Graham and Van der Eb (1973).

The permissive cell line 293 is a human kidney cell line containing a functional E1a gene that provides a trans-acting E1a protein (Graham et al., 1977)] and high-titer, infectious Ad-CFTR viral stocks were prepared.

Viral DNA was isolated (Hirt, 1967), and recombinant adenovirus plaques containing the human CFTR cDNA (Ad-CFTR) were identified by restriction cleavage and Southern analysis. Ad-CFTR and the control viruses Ad-alpha IAT (Rosenfeld et al., 1991a) and the E1a deletion virus Ad-d1312 (Jones and Shenk, 1979) were propagated in 293 cells and recovered 36 hr after infection by 5 cycles of freeze/thawing. All viral preparations were purified by isopycnic cesium chloride (CsCl) density centrifugation (Graham and Van Der Eb, 1973), dialysed and stored in by isopycnic cesium chloride (CsCl) density centrifugation (Graham and Van Der Eb, 1973), dialysed and stored in 10 mM Tris-HCL, pH 7.4, 1 mM ,MgCl, 10% glycerol at −70° C. prior to use. Titers of the viral stocks were determined by plaque assay using 293 cells (Graham and Van Der Eb, 1973; Graham et al., 1977).

EXAMPLE 2

1) In vitro evaluation of Ad-CFTR Directed Human CFTR mRNA Transcripts

Figure 3:
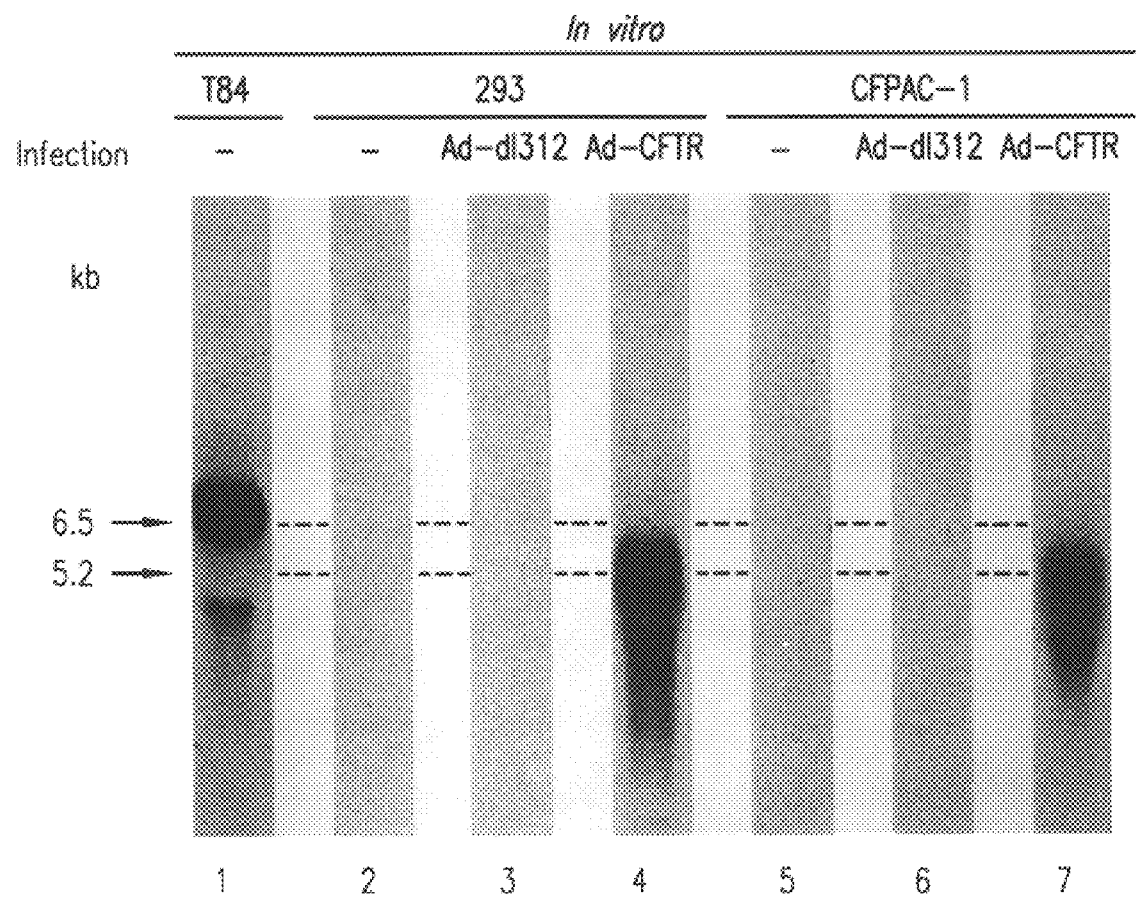
FIG. 3 represents the evaluation of human CFTR mRNA transcripts after Ad-CFTR infection both in vitro and in vivo reported in example 21. Shown are northern analyses of total cellular RNA (10 μg/lane except for 293 cells 5 μg/lane) evaluated with a 4.5 kb human CFTR cDNA probe. Lanes 1–7 are studies with RNA from cells infected in vitro and lanes 8–9 utilize RNA from the lungs of a cotton-rat infected in vivo. Lane 1—uninfected T84 cells lane 2—uninfected 293 cells; lane 3—293 cells infected with Ad-d1312; lane 4—293 cells infected with Ad-CFTR; lane—uninfected CFPAC-1 cells; lane 6—CFPAC-1 cells infected with Ad-d1312; lane 7—CFPAC-1 cells infected with Ad-CFTR; lane 8—uninfected cotton rat lung; and lane 9—cotton rat lung 2 d after infection with Ad-CFTR. The 6.5 kb endogenous human CFTR mRNA transcripts are indicated, as are the 5.2 kb Ad-CFTR-directed CFTR mRNA transcripts. The latter are expected to be smaller than the endogenous human cell transcripts due to deletion of 5' and 3' untranslated sequences from the CFTR cDNA in the construction of Ad-CFTR (see FIG. 1).

Ad-CFTR directed expression of human CFTR mRNA transcripts both in vitro and in vivo (FIG. 3). As previously observed, northern analysis of T84 human colon carcinoma cells demonstrated 6.5 kb CFTR mRNA transcripts (Riordan et al., 1990; Kartner et al., 1991; Yoshimura et al., 1991; Trapnell et al., 1991a) (lane 1) while uninfected 293 or CFPAC-1 cells did not contain detectable CFTR MRNA transcripts using the 4.5 kb human CFTR probe (lanes 2, 5, respectively). Similarly, in vitro infection of 293 cells (lane 3) or CFPAC-1 cells (lane 6) by the control virus Ad-d1312 [Ad 5 with a deletion of the E1a region (1.5 to 4.5 mu; Jones and Shenk, 1979)] which does not contain the CFTR cDNA did not demonstrate detectable CFTR transcripts. In contrast, 5.2 kb transcripts (the expected size of Ad-CFTRdirected human mRNA transcripts) were observed after in vitro Ad-CFTR infection of 293 cells (lane 4) or CFPAC-1 cells (lane 7). The levels of human beta-actin transcripts were similar in all samples. Importantly, Ad-CFTR-directed human CFTR mRNA transcripts of a size similar to that directed by Ad-CFTR in cultured cells, were observed in total lung RNA 48 hrs after in vivo infection of cotton rats by intratracheal instillation of Ad-CFTR (lane 9), but not in uninfected animals (lane 8). Levels of cotton rat glyceraldehyde-3phosphate dehydrogenase transcripts were similar for both samples.

2) In vitro function of the Ad-CFTR-Directed Human CFTR Protein

As there is no animal model for cystic fibrosis, it is not possible to evaluate the function of the Ad-CFTR-directed CFTR protein in vivo. However, the Ad-CFTR vector clearly directed the biosynthesis of functional CFTR protein as demonstrated by in vitro studies in cultured cells (FIG. 5). In this regard, the de novo biosynthesis of human CFTR protein was evaluated in cells modified in vitro by Ad-CFTR infection using metabolic labeling and immunoprecipitation of the CFTR protein with a mouse anti-human CFTR-specific monoclonal antibody. Evaluation of Ad-CFTR infected 293 cells demonstrated the presence of a new 165 kDa protein, and a minor 141 kDa protein (panel A, lane 2) neither of which were present in uninfected cells (lane 1). CFPAC-1 cells infected by Ad-CFTR also showed a new protein band of 165 kDa (lane 4) not present in Ad-alpha1AT infected (lane 3) or uninfected cells. For both 293 and CFPAC-1 cells, the size of the major Ad-CFTR-directed protein (165 kDa) is within the range of the size detected in T84 cells and that expected for a completely processed form of the glycosylated protein. (Riordan et al., 1989, Cheng et al., 1990, Kartner et al., 1991).

The ability of Ad-CFTR to impart cAMP-regulated Cl⁻ secretion to cells which do not normally exhibit cAMP-regulated Cl⁻ secretion (293 cells) and to correct the defective cAMP-stimulated upregulation of Cl⁻ secretion in epithelial cells derived from individuals with cystic fibrosis (CFPAC-1 cells) was evaluated by examining forskolin-stimulated $^{36}$Cl⁻ efflux (FIG. 5, panels B–F). Consistent with the lack of detectable endogenous CFTR mRNA expression, uninfected 293 cells lacked the ability to upregulate Cl⁻ secretion in the presence of forskolin (panel B). In contrast, after Ad-CFTR infection, forskolin significantly stimulated Cl⁻ secretion (panel C). As expected, uninfected CFPAC-1 cells (panel D) or CFPAC-1 cells infected with the control virus Ad-alpha1AT (panel E) did not demonstrate forskolin-stimulated Cl⁻ secretion. However, after in vitro infection with AdCFTR, CFPAC-1 cells had a significant increase in forskolin-stimulated Cl⁻ secretion (panel F) indicating correction of the CF eipthelial cell phenotype and thus the function of the Ad-CFTR-directed product.

3) Expression of Ad-CFRT Directed Human CFTR mRNA in Bronchial Epithelium In-vivo Following intratracheal administration of the Ad-CFTR vector of example 1 in cotton rats in vivo, the presence of human CFTR mRNA transcripts could be detected in bronchial epithelium by in situ hybridization analysis using human CFTR cRNA probes (FIG. 2). Control animals not infected with Ad-CFTR did not show hybridization with the antisense probes (Panel A). In contrast, hybridization of the antisense probes demonstrated expression of human CFTR mRNA sequences diffusely throughout the epithelium of the airways of animals infected with Ad-CFTR (panels C, E, G). As a further control, sense probes did not show hybridization in bronchial tissues from uninfected (panel B) or Ad-CFTR infected cotton rats (panels D, F, H). The absence of hybridization with the sense probes in the lung of AdCFTR-infected animals also indicated that any residual Ad-CFTR DNA that might be present in the tissue was not detectable by the methods utilized.

Figure 4A:
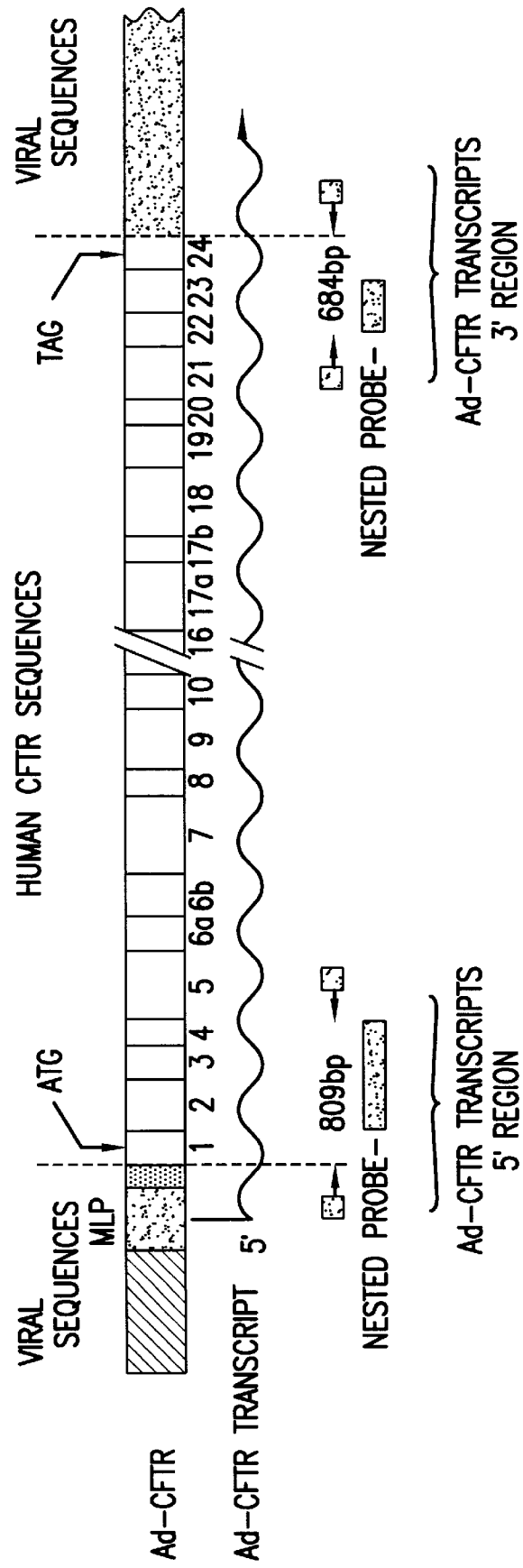
FIGS. 4A–E represents evaluation of the chronicity of human CFTR gene expression-in cotton rat lung following in vivo infection with Ad-CFTR reported in example 2—2. A. Schematic of a portion of Ad-CFTR showing the Ad-CFTR-derived CFTR mRNA transcript and the location of primer pairs used to identify the Ad-CFTR-directed mARN transcripts specifically. Ad-CFTR DNA sequences shown include (from the left) adenoviral expression cassette sequences (see FIG. 1 for details) including the major late promoter (MLP), the human CFTR cDNA coding sequence (CFTR exons are indicated by numbers below Ad-CFTR), and the remainder of the adenoviral vector genome. The Ad-CFTR transcript 5' amplification primer pair consists of a 5' viral-specific sense primer and a 3' human CFTR cDNA-specific antisense primer. The 3' primer pair consists of a 5' human CFTR cDNA-specific sense primer and a 3' viral-specific antisense primer. Also shown are the sizes of the expected amplification products and the "nested" probes used to detect specifically amplified Ad-CFTR transcripts. mRNA was converted to cDNA and amplified as described in Methods. Panels B–E—mRNA transcripts in cotton rat lung following in vivo infection with Ad-CFTR. "−" and "+" indicate the absence and presence of reverse transcriptase (RT), respectively, in the cDNA synthesis reactions. The sizes of expected amplification products are indicated in each panel. Panel B. Evaluation of the 5' region of Ad-CFTR-directed mRNA transcripts. Lane 1—uninfected coton rat lung RNA without RT; lane 2—same as lane 1, with RT; lane 3—2 d after infection with Add1312, without RT; lane 4—same as lane 3, but with RT; lane 5—2 d after infection with Ad-CFTR, without RT; lane 6—same as lane 5, with RT. Panel C. Evaluation of rat glyceraldehyde-3-phosphate dehydrogenase (GAPDH) mRNA transcripts. Lane 7—uninfected cotton rat lung RNA, without RT; lane 8—same as lane 7, with RT; lane 9—2 d after infection with Ad-d1312, without RT; lane 10—same as lane 9, with RT; lane 11—2 d after infection with Ad-CFTR, without RT; lane 12—same as lane 11, with RT. Panel D. Evaluation of the 5' region of Ad-CFTR-derived CFTR mRNA transcripts in cotton rat lung after infection with Ad-CFTR. Lane 13—2 wk after infection, without (RT); lane 14—same as lane 13, with RT; lane 15—4 wk after infection, without RT; lanes 16—same as lane 15, with RT; lane 17—6 wk after infection, without RT; lane 18—same as lane 17, with RT. Panel E. 3' region amplification of CFTR in cotton rat lung after infection with Ad-CFTR. Lane 19—2 wk after infection, without-(RT); lane 20—same as lane 19, with RT; lane 21—4 wk after infection, without RT; lane 22—same as lane 21, with RT; lane 23—6 wk after infection, without RT; lane 24—same as lane 23, with RT.
Figure 4B:
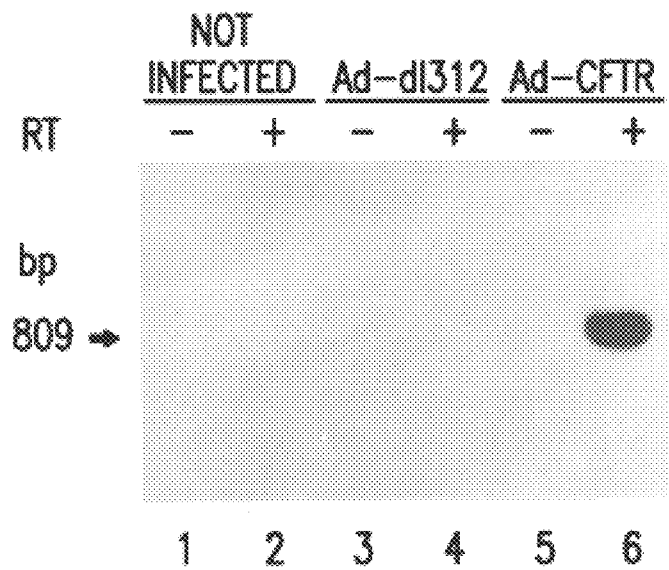
Figure 4C:
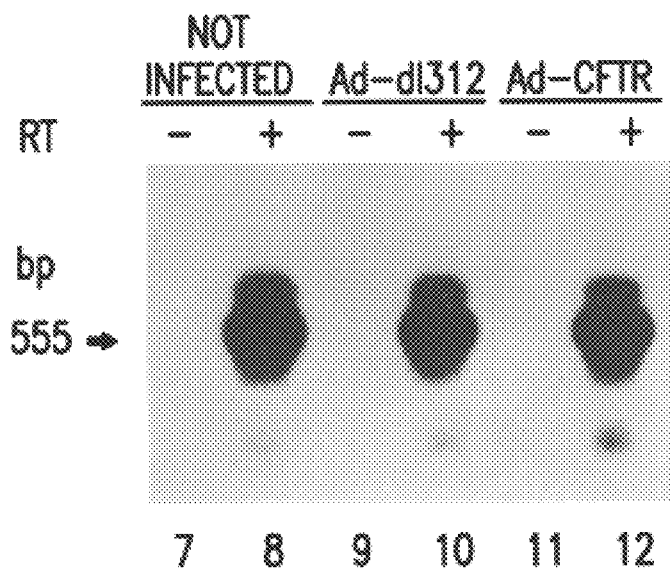
Figure 4D:
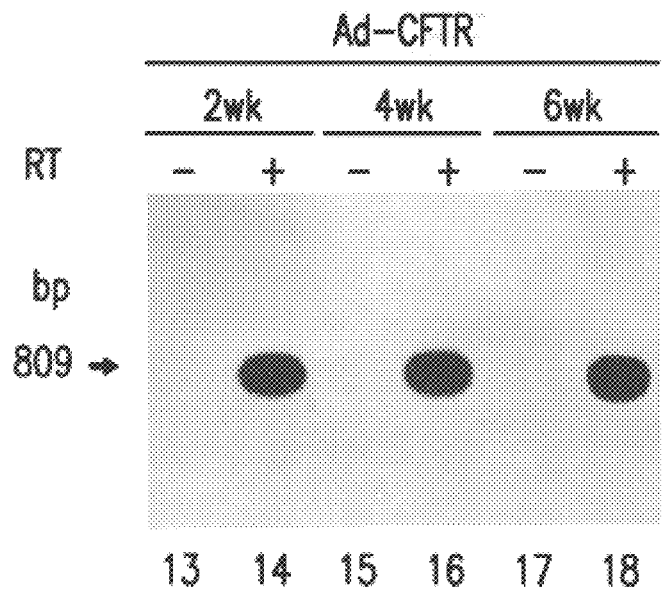
Figure 4E:
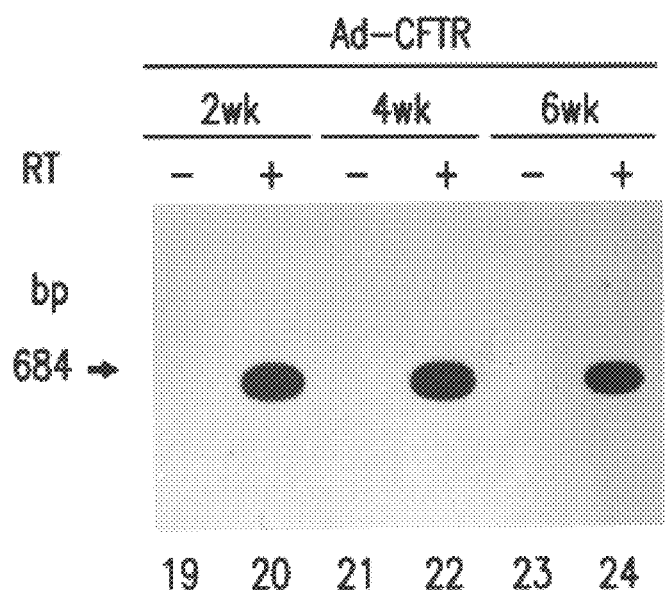
Figure 5A:
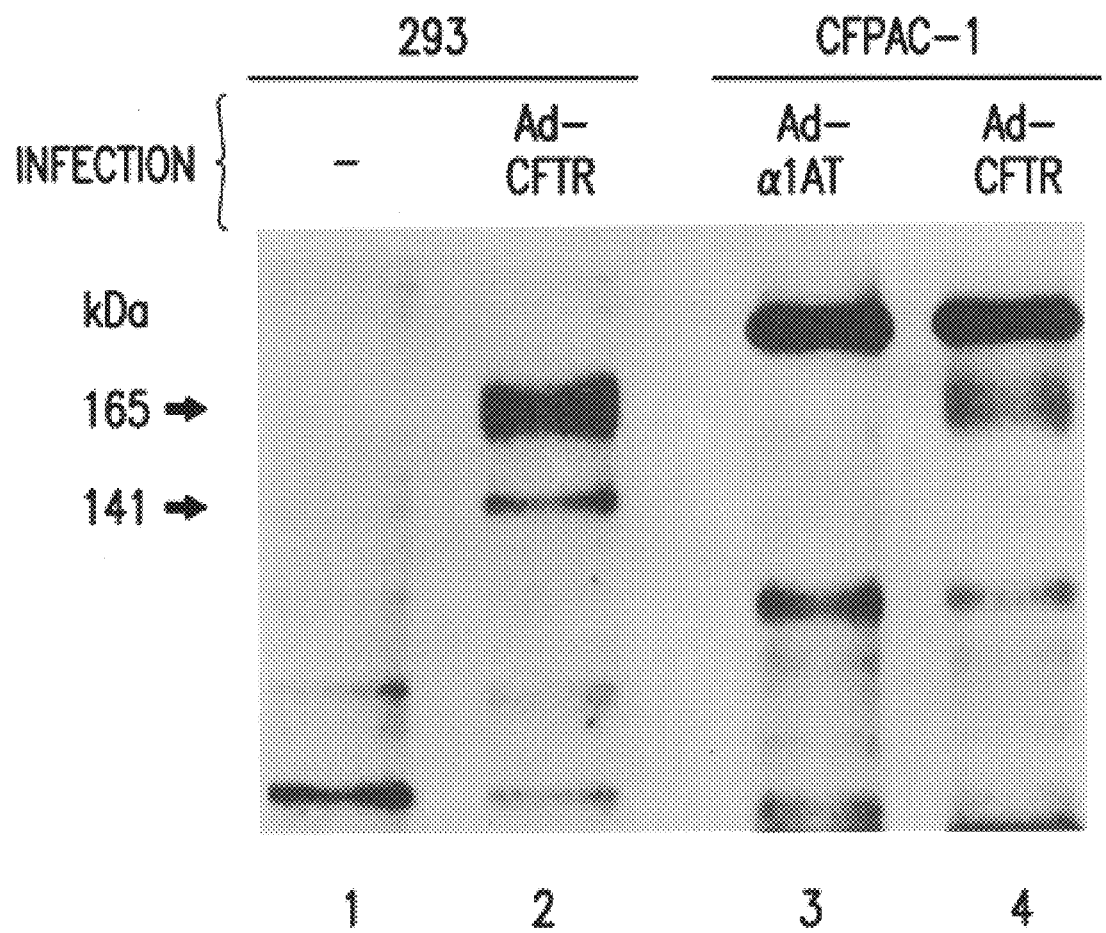
FIGS. 5A–F represents in vitro evaluation of the size, form and function of the human CFTR protein directed by Ad-CFTR reported in example 2-3. Panel a. De novo biosynthesis of human CFTR. Cells were infected, labeled with [$^{35}$S]methionine, and then evaluated for $^{35}$Slabeled CFTR by immunoprecipitation as described in the Methods. Lane 1—uninfected 293 cells; lane 2—293 cells after infection with Ad-CFTR; lane 3—CFPAC-1 cells infected with the control virus Ad-alpha1AT; lane 4—CFPAC-1 cells infected with Ad-CFTR. The major 165 kDa CFTR protein and minor 141 kDa bands are indicated. Panels B–F. Evaluation of the functional ability of Ad-CFTR-derived human CFTR to modulate forskolin-stimulated Cl⁻ secretion. $^{36}$Cl⁻ efflux was evaluated at rest (basal) and after stimulation (forskolin) as described in the Methods. The data are presented as % Cl⁻ remaining in cells at each time point under basal or forskolin-stimulated conditions; each data point represents the mean of separate determinations (for each data point in panels B, C, and E, n-3; in panels D and F, n-4).
Figure 5B:
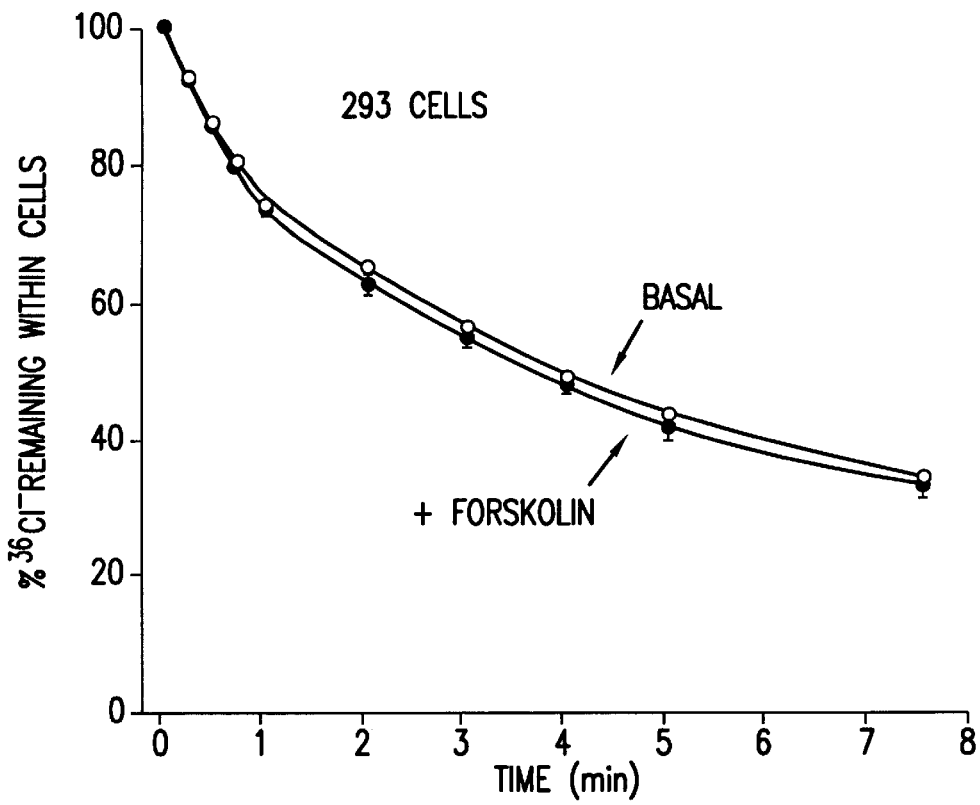
Figure 5C:
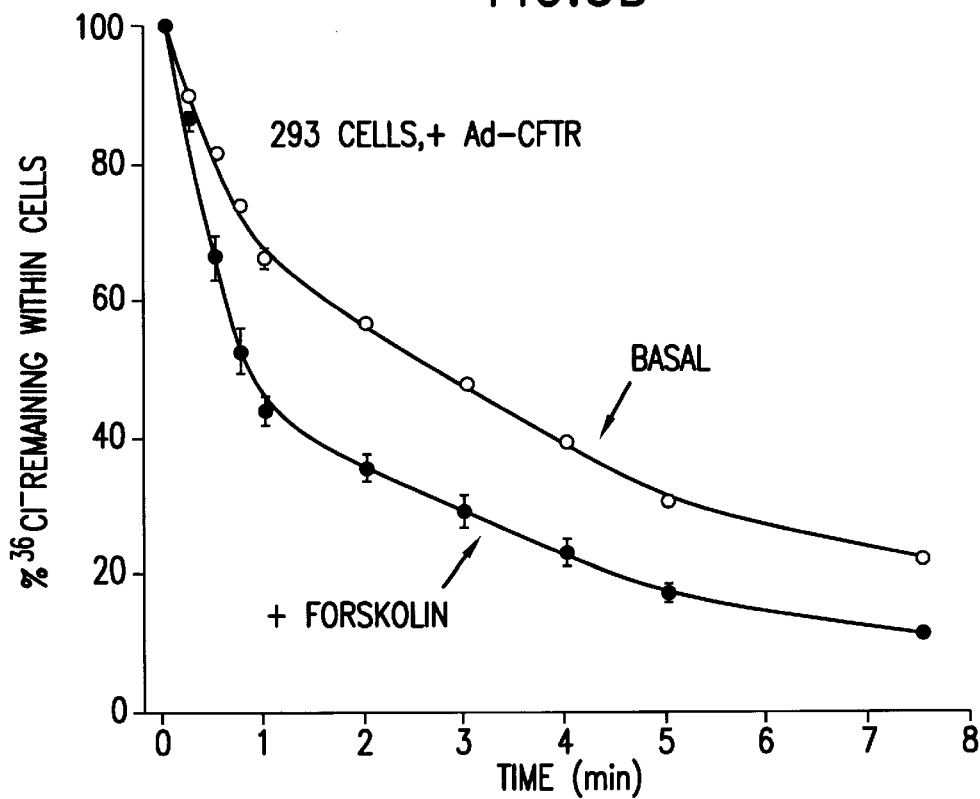
Figure 5D:
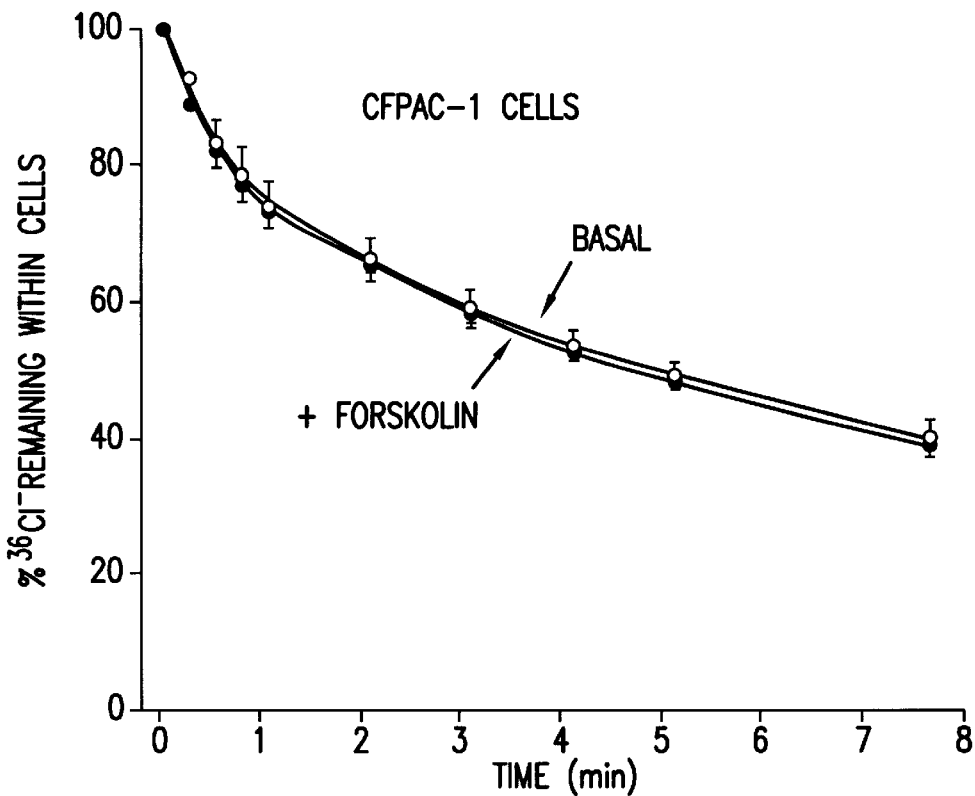
Figure 5E:
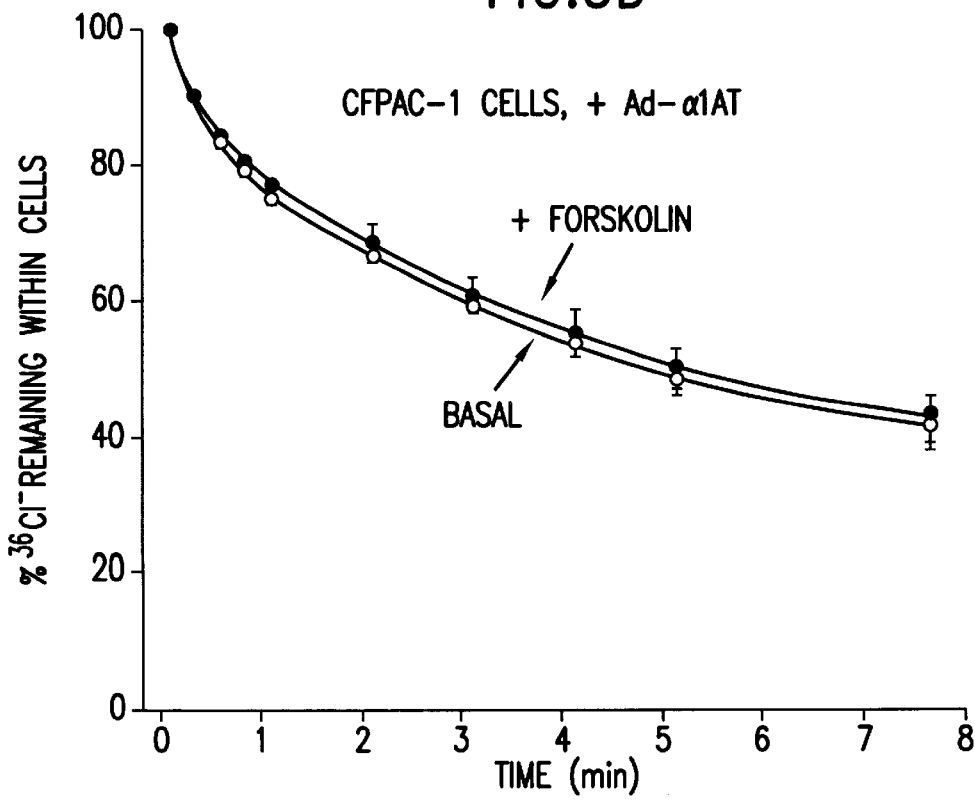
Figure 5F:
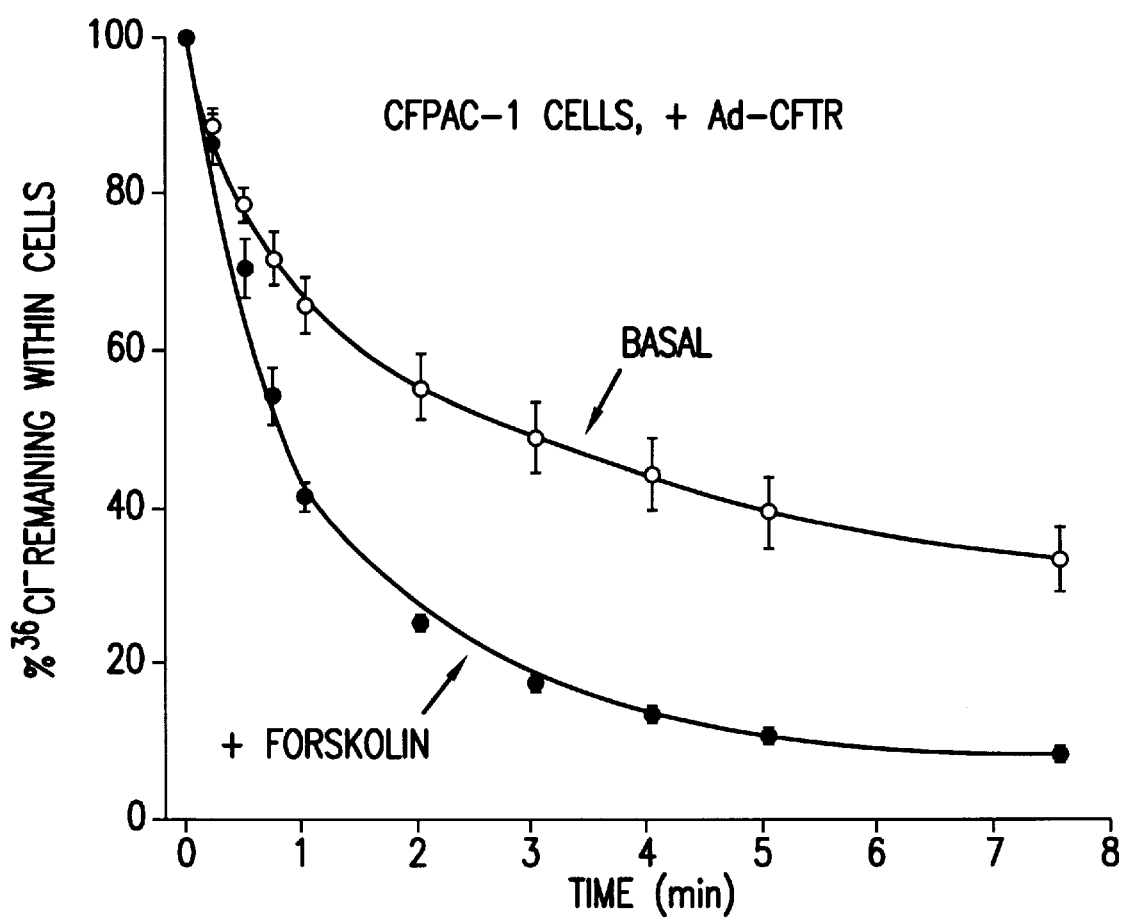
Figure 6A:
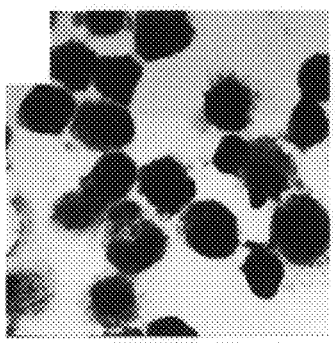
Figure 6B:
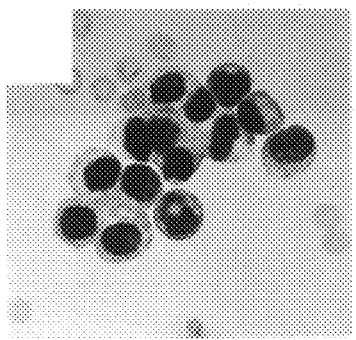
Figure 6C:
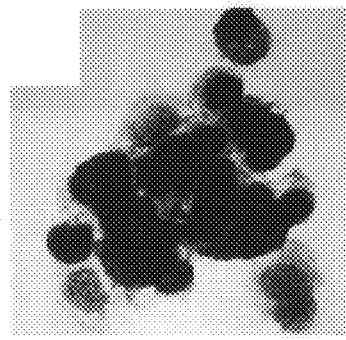
Figure 6D:
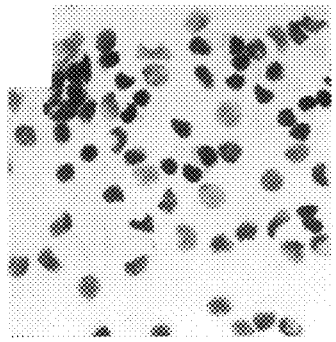
Figure 6E:
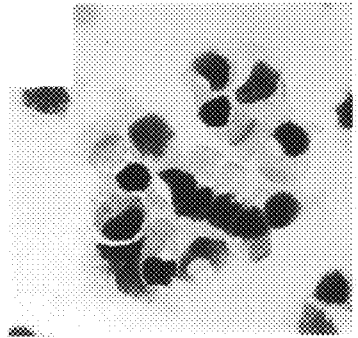
Figure 6F:
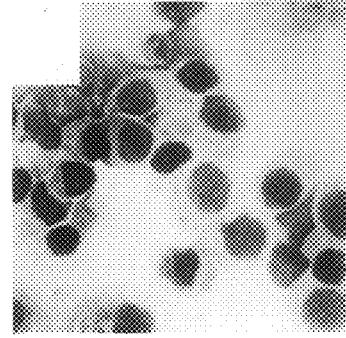
Figure 6G:
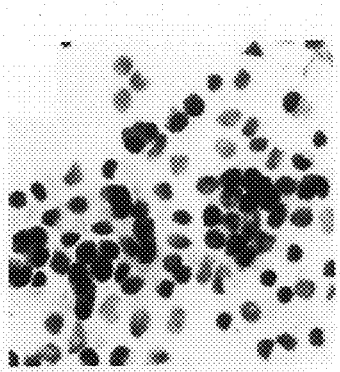
Figure 6H:
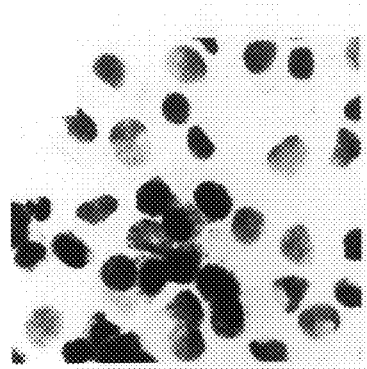
Figure 6I:
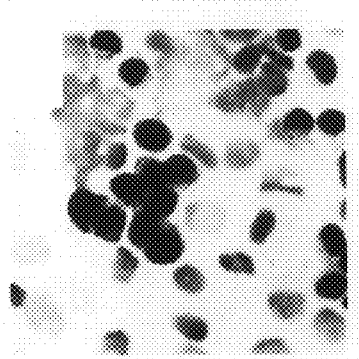
Figure 6J:
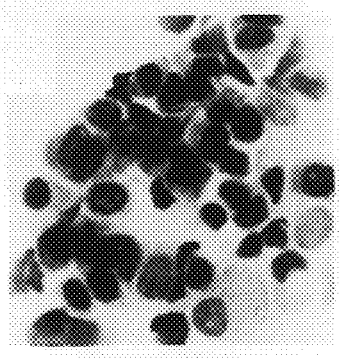
Figure 6K:
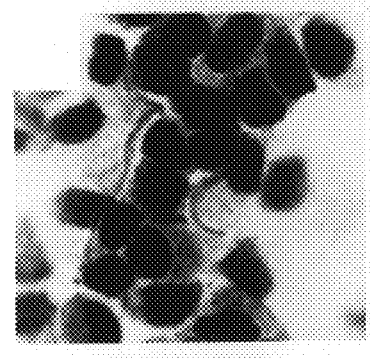
Figure 6L:
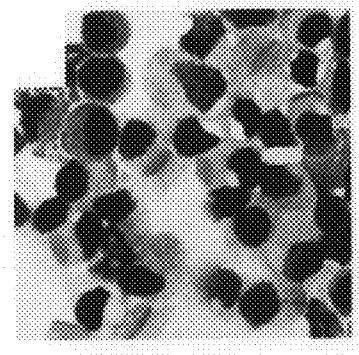

4) Specificity and Chronicity of Expression of Human CFTZ mRNA Transcripts Following In Vivo Infection To further confirm the presence of human CFTR mRNA transcripts in the lungs of cotton rats infected with Ad-CFTR a strategy was employed which allows detection of only those transcripts with contiguous viral and human RNA sequences expected to be directed by Ad-CFTR. This was accomplished by amplification of Ad-CFTR mRNA (after conversion to cDNA) using the polymerase chain reaction (PCR) with two pairs of primers: (1) an adenoviral sense primer for viral sequences 5' to the viral/human CFTR junctional sequences and an opposing human CFTR cDNA antisense primer located within human CFTR exon 5; and (2) a human CFTR cDNA sense primer located within exon 21 and a viral antisense primer for SV40 viral sequences 3' to the human/viral RNA junctional sequences (FIGS. 1, 4A). To ensure that only RNA sequences were being detected and to exclude detection of potentially contaminating Ad-CFTR DNA, RNA samples were exposed to DNase I prior to conversion of purified RNA to cNDA and subsequent PCR. Further, each sample was evaluated in the absence or presence of reverse transcriptase. Ad-CFTR-directed human CFTR transcripts were detected using the 5' region primer-pair after Ad-CFTR infection, but not in uninfected animals or after Ad-d1312 infection (panel B). In the absence of reverse transcriptase, none of the samples amplified CFTR mRNA sequences. As a control, rat glyceraldehyde-3-phosphate dehydrogenase mRNA transcripts were detected in rat lung total RNA in all samples after incubation with reverse transcriptase, but not in the absence of reverse transcriptase (panel C).

The chronicity of Ad-CFTR-directed CFTR mRNA expression was demonstrated in cotton rat lung evaluated 2, 4, and 6 wk after in vivo infection with Ad-CFTR. Ad-CFTR-directed transcripts were observed at all time points with the 5' region amplification (panel D) and also with the 3' region amplification (panel E). In the absence of reverse transcriptase, no samples showed amplification of CFTR sequences.

5) Detection of Human CFTR Protein after in Vivo Adenovirus-Medisted Gene Transfer Immunohistochemical evaluation with an anti-human CFTR antibody demonstrated human CFTR protein in cotton rat respiratory epithelial cells following in vivo intratracheal installation of Ad-CFTR (FIG. 6). As a control, the anti-CFTR antibody demonstrated human CFTR protein in T84 cells (a cell fine known to express CFTR; FIG. 6A). Human CFTR was not found in uninfected cotton rat respiratory epithelial cells evaluated in vitro (FIG. 6B), but was present in cotton rat respiratory epithelial cells infected in vitro with Ad-CFTR (7C). Human CFTR protein was not detected in cotton rat respiratory epithelium of uninfected animals (FIGS. 6D and 6E), or animals infected with the control virus Ad-d1312 (6F). Importantly, human CFTR protein was detected in cotton rat respiratory epithelial cells 11–14 days after in vivo infection with Ad-CFTR (FIGS. 6G–7K), but not when the primary antibody was omited (6L), or when the primary antibody was replaced by an irrelevant antibody of the same antibody subclass (data not shown).

METHODS

Cell Cultures

The transformed human embryonic kidney cell line 293 [American Type Culture Collection (ATCC) CRL 1573 (Graham et al., 1977);] was grown in Improved minimal essential medium (Biofluids Inc.) containing 10% fetal bovine serum (FBS, 2 mM glutamine, 50 units/ml penicillin, and 50 µg/ml streptomycin. CFPAC-1 cells, originally derived from a pancreatic adeno-carcinoma of an invididual homozygous for the common deltaF508 CF mutation (Schoumacher et al., 1990), were grown in ulbecco's modified Eagle's medium (DMEM, Biofluids) with supplements as above. The human colon adenocarcinoma cell line T84 (ATCC CCL 248) was cultured as for CFPAC-1 cells, except with 5% FBS.

In Vitro and In Vivo Infection with Ad-CFTR

For in vitro infection, the cells were trypsinized, counted, seeded [10 cm plates ($4.5 \times 10^6$ cells/plate) for evaluation of CFTR mRNA or synthesis of CFTR protein; 6 cm plates ($5.0 \times 10^5$ cells/plate) for evaluation of $Cl^-$ secretion in response to forskolin] and infected with Ad-CFTR, Ad-d1312, or Ad-alpha1AT (200 plaque forming units (PFL) per cell for CFPAC-1 cells; 50 PFU per cell for 293 cells). After 18 to 24 hr (for 293 cells) or 48 hr (for CFPAC-1 cells), cells were evaluated for CFTR mRNA, synthesis of CFTR protein, and $Cl^-$ secretion in response to forskolin (see below). For in vivo studies, cotton rats (Sigmodon hispidus) were anesthetized by methoxyfluorane inhalation. The trachea was exposed by anterior midline incision and $10^{10}$ PFU of Ad-CFTR or Ad-d1312 were injected into the trachea in a total volume of 300 µl of phosphate buffered saline, pH 7.4 (PBS). An equal volume of PBS (with glycerol at the concentration contained in the viral preparation used for the infection) was injected in other cotton rats as an additional negative control.

Virus used immediately after dialysis was not diluted, and thus, corresponding control animals received an equal volume of the virus dialysis buffer containing 10 mM Tris-HCl (pH 7.4), 1 mM $MgCl_2$.

Northern Analysis of CFTR mRNA Transcripts

For in vitro infection experiments, total RNA was isolated from 293 cells or CFPAC-1 cells (at 20 and 48 hr after adenoviral vector infection, respectively) or as a control from uninfected subconfluent T84 cells, using the guanidine thiocyanate-CsCl technique (Chirgwin et al., 1979). For in vivo studies, cotton rats were evaluated two d to 6 wk after infection. The lungs were isolated as described after. Following exanguination by cardiac puncture, the lungs were lavaged twice, the pulmonary artery was perfused with PBS and the lungs and trachea were resected, minced and total lung RNA was extracted (Chirgwin et al., 1979; Rosenfeld et al., 1991a).

RNA was subjected to formaldehyde-agarose gel electrophoresis, transferred to a nylon membrane (Nytran, Schleigher & Schuell), hybridized with a $^{32}P$-labeled, 4.5 kb CFTR cDNA probe prepared by random priming and evaluating by autoradiography as previously described (Yoshimura et al., 1991). As a control, the same membranes were subsequently hybridized with either a human beta-actin cDNA probe [pHFbetaA-1, for cultured human cells (Gunning et al., 1983)] or a rat glutaldehyde-3-phosphate dehydrogenase (GAPDH) cDNA probe [for rat lung RNA (Tso et al., 1985)].

In Vitro Evaluation of the Function of Ad-CFTR-Derived Human CFTR

In vitro synthesis of human CFTR was evaluated in 293 and CFPAC-1 cells after Ad-CFTR infection. Cells were incubated in labelling medium [methionine-free LHC-8 medium (Biofluids) containing [$^{35}S$]methionine (500 µCi/ml; 1000 Ci/mmol, New England Nuclear] during the entire infection period. After infection (24 h for 293 cells; 48 hr infection for CFPAC-1 cells) cells were washed twice in PBS, and solubilized at 4° in lysis buffer [PBS containing 10 mM ethylenediaminetetraacetate, 1% Triton X-100, 0.5% sodium deoxycholate, 200 µg/ml aprotinin, 100 µg/ml leupeptin (both from Boehringer Mannheim), and 2 mM phenymethylsulfonyl fluoride, (Sigma)]. The cell lysate was frozen (–70° for at least 30 min), thawed and clarified by centrifugation (12,000 g, 4°, 30 min); for each 293 cell sample $3 \times 10^6$ dpm and for each CFPAC-1 cell sample $30 \times 10^6$ dpm total trichloracetic acid precipitable radioactivity was used to evaluate $^{35}S$-labeled human CFTR by immunoprecipitation with a mouse anti-human CFTR monoclonal antibody (Genzyme), followed by sodium dodecyl sulfate (SDS)-polyacrylamide gel electrophoresis and fluororadiography (Mornex et al., 1986; Rosenfeld et al, 1991a).

To demonstrate that the Ad-CFTR vector was capable of directing the expression of functional CFTR protein, forskolin-stimulated $Cl^-$ secretion was evaluated in cells that do not normally exhibit cAMP-mediated $Cl^-$ secretion (293 cells) or in human epithelial cells derived from an individual with CF [CFPAC-1 cells, a cell line homozygous for deltaF508 CF mutation (Schoumacher et al., 1990)]. To accomplish this, at 18 hr (293 cells) or 48 hr (CFPAC-1 cells) after infection with Ad-CFTR, $Cl^-$ efflux was evaluated (Trapnell et al., 1991a). Monolayers of 293 or CFPAC-1 cells were washed twice with Ringer's lactate and loaded with $^{36}Cl^-$ (2.5 µCi/ml; >3 mCi/gram Cl, Amersham; 2 hours, 37°) and then washed rapidly with 3 ml aliquots (×6) of Ringer's lactate buffer. $^{36}Cl^-$ efflux was measured by sequentially removing and replacing buffer (0.9 ml aliquots) at various time intervals for up to 7.5 min. The cells were then removed from the dish with 0.9 ml of 0.25% trypsin (Biofluids) and the amount of $^{36}Cl^-$ in the efflux aliquots and cells determined by liquid scintillation counting. The total radioactivity loaded into cells was calculated from the sum of the individual efflux time points plus that remaining in cells at the end of the sampling period. $Cl^-$ efflux data were plotted for each time point as $^{36}Cl^-$ remaining in cells as a percentage of total $^{36}Cl^-$ initially loaded into cells. Forskolin stimulated $Cl^-$ secretion was evaluated by adding 13 µM forskolin (Sigma, St. Louis, Mo.), to the sampling buffer used for collection of the efflux samples.

Analysis of CFTR mRNA Expression by In Situ Hybridization

Cotton rats lungs and trachea were isolated as described above. After blood was removed by cardiac puncture, the lungs were fixed with 4% paraformaldehyde (PFA, Fluka) infused into the trachea and pulmonary artery. Cyrostat sections (7 to 10 µm) were prepared, cut and stored frozen (–70°) until use. Immediately prior to hybridization, cryostat sections were sequentially treated with 0.2M HCL and 1 µg/ml proteinase K. Three different sets of human CFTR $^{35}S$-labeled sense and antisense cRNA probes were synthesized in vitro from plasmid transcription vectors (pGEM, Promega) with [$^{35}S$]UTP (1 mCi, 800 Ci/mmol, SP6/T7 grade; Amersham) by standard techniques. Each pGEM CFTR vector contained a different region of human CFTR cDNA (exons 1–5, 9–13, or 21–24). These probes were combined, hydrolyzed and the lung tissue sections were then hybridized (12 hr, 50 G) with the labeled cRNA probes (1.2×10$^5$ dpm/μl). Lung tissue sections were then washed, treated with RNase A (50 μg/ml, Sigma), washed, dehydrated, and evaluated by autoradiography (10 d) and counterstained with hemotoxylin and eosin (Harper et al., 1986; Bernaudin et al., 1988, Rosenfeld et al., 1991a).

Relative expression of human CFTR mRNA in epithelium versus subepithelium was determined by calculating the mean number of silver grains over these areas, subtracting the mean background grains from each (defined as number of silver grains in cell-free areas), and expressing this value as a ratio of expression in epithelium versus subepithelium.
Detection of CFTR mRNA Transcripts Using the Polymerase Chain Reaction Ad-CFTR-directed mRNA transcripts were evaluated in rat lung RNA (prepared as above) after conversion to CDNA, PCR amplification and Southern hybridization analysis. RNA was first treated with DNase (10 units/μg RNA; RNase-free RQ1 DNase, Promega) to eliminate possible residual viral DNA. RNA was then converted to cDNA by standard techniques using Moloney murine leukemia virus reverse transcriptase (RT) with random hexanucleotide primers (Roth et al., 1985) and amplified by PCR (25 cycles) and Taq DNA polymerase [Perkin Elmer Cetus; (Saiki et al., 1988)]. To insure that Ad-CFTR driven transcripts were specifically evaluated and that the 5' and 3' portions of the mRNA transcripts were present, two separate primers-pairs were used: a 5' primer pair to detect the 5' end of Ad-CFTR mRNA transcripts consisting of an adenoviral-specific sense primer in the tripartite leader sequence (VAD-5; 5'-AGCTGTTGGGGCTCGCGGTTGAGG-3') (SEQ ID NO: 1) and a human CFTR-specific antisense primer in CFTR exon 5 (HCF60; 5'-CATCAAATTTGTTCAGGTTGTTGG-3') (SEQ ID NO: 2); and a 3' primer pair to evaluate the 3' end of Ad-CFTR mRNA transcripts consisting of a human CFTR-specific sense primer in CFTR exon 21 (HCF12; 5'-AGTGGAGTGATCAAGAAATATGG-3'(SEQ ID NO: 3) and an SV40 viral-specific primer in the SV40 early mRNA polyadenylation signal sequence (SVPOLYA; 5'-GTAACCATTATAAGCTGCAATAAAC-3'(SEQ ID NO: 4); Fiers et al., 1978). As a control, rat GAPDH transcripts corresponding to amino acid residues 126 to 300 were amplified under similar conditions using GAPDH transcript-specific primers [(GAPDH-1; 5'-AATGCATCCTGCACCACCAACTGC-3') (SEQ ID NO: 5) and (GAPDH-2; 5'-GGAGGCCATGTAGGCCATGAGGTC-3'(SEQ ID NO: 6); Tso et al., 1985)]. Each DNase-treated RNA sample was also used as a PCR template in parallel without conversion to cDNA to eliminate the possibiliby that amplification of potentially contaminating viral DNA occurred. PCR amplification products were evaluated by agarose gel electrophoresis followed by Soughern hybridization using nested or internal $^{32}$P-labeled CFTR cDNA probes [a 462 bp PvuII-XbaI fragment spanning exons 2 to 5 (Riordan et al., 1989) for the 5' region amplification products, or a 200 bp fragment spanning exons 22 to 23 (Riordan et al., 1989 ; Yoshimura et al., 1991; Trapnell et al., 1991a) for the 3' region amplification products]; or an internal rat GAPDH cDNA probe [a 281 bp BanII fragment within the amplified GAPDH transcript region described above (Tso et al., 1985)].
Immunohistochemical Detection of the Human CFTR Protein after in Vivo Infection with Ad-CFTR Human CFTR was evaluated in cytocentrifuge preparations of cotton rat lung epithelium infected in vitro or obtained from cotton rat lung 11–14 days after in vivo Ad-CFTR intratracheal instillation using the alkaline phosphatase monoclonal anti-alkaline phosphatase (APAAP) method (Cordell et al., 1984) and anti-human CFTR antibody (Genzyme) with minor modifications. Briefly, for in vitro studies, cells were collected 48 hr after in vitro infection with the recombinant adenovirus and resuspended in Hanks balanced salt solution (HBS, Mediatech) supplemented with 2% heat-inactivated fetal calf serum (Biofluids), and cytoprep slides were prepared by cytocentrifugation (450 rpm, 3 min). For the in vivo studies, the airway epithelial cells were obtained from cotton rats as described above and immediately cytocentrifuged. As controls, T84 cells were trypsinized and prepared in the same manner. Air-dried slides were evaluated immediately or stored at −70° C. until evaluation. Cytopreps were fixed in acetone for 10 min at −20° C. and air-dried. Cells were first incubated with a mouse anti-human CFTR monoclonal antibody raised against a CFTR exon 13-beta-galactosidase fusion protein (1 μg/ml, Genzyme) in the presence of protease inhibitors (100 μg/ml aprotinin, 50 μg/ml leupeptin, 15 μg/ml chymostatin, 0.675 mM phenylmethylsulfonyl fluoride [all from Boehringer Mannheim], 7.5 μg/ml pepstatin [Cal Biochem], 1,5 mM p-aminobenzoic acid [Fluka]). Slides were subsequently incubated with rabbit anti-mouse immunoglobulin (96 μg/ml, Dako), followed by alkaline phosphatase mouse monoclonal anti-alkaline phosphatase (6,8 μg/ml, Dako). The intensity of immunoreactivity was enhanced by repeating the last two antibody incubation steps. Immuno-reactivity was detected using a simultaneous capture azo-dye technique (Histo-Mark™ Red test system, Kirkgaard & Perry). As controls, duphocate slides were evaluated in the absence of the primary anti-human CFTR antibody or with an irrelevant primary mouse monoclonal antibody (anti-human Leu-2A(CD8), Becton Dickinson).

REFERENCES

1. Anderson, M. P., Rich, D. P., Gregory, R. J., Smith, A. E. and Welsh, M. J. (1991 *Science*, 251, 679–682.
2. Berkner, K. L. (1988) *Biotechniques*, 6, 616–629
3. Bernaudin, J-F., Yamauchi, K., Wewers, M. D., Tocci, M. J., Ferrans, V. J. and Crystal, R. G. (1988) *J. Immunol.*, 140, 3822–3829.
4. Boat, T. F., Welsh, M. J. and Beaudet, A. L. (1989) In Scriver, C. R., Beaudet, A. L., Sly, W. S. and Valle, D. (eds.) *The Metabolic Basis of Inherited Disease*. McGraw-Hill, New York, 6th ed., pp.2649–2680.
5. Cheng, S. H., Gregory, R. J., Marshall, J., Paul, S., Souza, D. W., White, G. A., O'Riordan, C. R. and Smith, A. E. (1990) *Cell*, 63, 827–834.
6. Chirgwin, J. M., Przybyla, A. E., MacDonald, R. J. and Rutter, W. J. (1979) *Bio-chemistry*, 18, 5294–5299.
7. Chu, C-S., Trapnell, B. C., Murtagh, J. J. Jr., Moss, J., Dalemans, W., Jallet, S., Mercenier, A., Pavirani, A., LeCocq, J-P., Cutting, G. R., Guggino, W. B. and Crystal R. G. (1991) *EMBO J.* 10, 1355–1363.
8. de Leval, M. R., Smyth, R., Whitehead, B., Scott, J. P., Elliott, M. J., Sharples, L., Caine, N., Helms P., Martin, I. R., Higenbottam, T. and Wallwork, J. (1991) *J. Thorac. Cardiovasc. Surg.*, 101, 633–642.
9. Drumm, M. L., Pope, H. A., Cliff, W. H., Rommens, J. M., Marvin, S. A., Tsui, L-C., Collins, F. S., Frizzell, R. A. and Wilson, J. M. (1990) *Cell*, 62, 1227–1233.
10. Evans, M. J. and Shami, S. G. (1989) In Lenfant, C. and Massaro, D. (eds.), *Lung Cell Biology*. Marcel Dekker, New York, pp. 1–36.

11. Fiers, W., Contreras, R., Haegeman, G., Rogiers, R., Van de Voorde, A., Van Heuverswyn, H., Van Herreweghe, J., Volckaert, G. and Ysebaert, M. (1978) *Nature*, 273, 113–120.
12. Frizzell, R. A., Rechkemmer, G. and Shoemaker, R. L. (1986) *Science*, 233, 558–560.
13. Graham, F. L. and Van Der Eb, A. J. (1973) *Virology*, 52, 456–467.
14. Graham, F. L., Smiley, J., Russell, W. C. and Nairn, R. (1977) *J. Gen. Virol.* 36, 59–72.
15. Gregory, R. J., Cheng, S. H., Rich, D. P., Marshall, J., Paul, S., Hehir, K., Ostedgaard, L., Klinger, K. W., Welsh, M. J. and Smith, A. E. (1990) *Nature*, 347, 382–386.
16. Gunning, P., Ponte, P., Okayama, H., Engel, J., Blau, H. and Kedes, L. (1983), *Mol. Cell. Biol.*, 782–795.
17. Haj-Ahmad, Y. and Graham, F. L. (1986) *J. Virol.*, 57, 267–274.
18. Harper, M. E., Marselle, L. M., Gallo, R. C. and Wong-Staal, F. (1986) *Proc. Natl. Acad. Sci. U.S.A.*, 83, 772–776.
19. Hirt, B. (1967) *J. Mol. Biol.*, 26, 365–369.
20. Horwitz, M. S. (1990) In Fields, B. N. and Knipe, D. M. (eds.), *Virology*. Raven Press, Ltd., New York, ed. 2, pp. 1679–1740.
21. Hwang, T. C., Lu, L., Zeitlin, P. L., Gruenert, D. C., Huganir, R. and Guggino, W. B. (1989) *Science*, 224, 1351–1353.
22. Jefferson, D. M., Valentich, J. D., Marini, F. C., Grubman, S. A., Ianuzzi, M. C., Dorkin, H. L., Li,M., Klinger, K. W. and Welsh, M. J. (1990) *Am. J. Physiol.* 259, L496–L505.
23. Jetton, A. M., Yankaskas, J.R., Stutts, M. J., Willumsen, N. J., Boucher, R. C. (1989) *Science*, 244, 1472–1475.
24. Jones, N. and Shenk, T. (1979) *Cell.* 17, 683–689.
25. Kartner, N., Hanrahan, J. W., Jensen, T. J., Naismith, A. L., Sun, S., Ackerly, C. A., Reyes, E. F., Tsui, L-C., Rommens, J. M., Bear, C. E. and Riordan, J. R. (1991) *Cell*, 64, 681–691.
26. Knowles, M., Gatzy, J. and Boucher, R. (1981) *N. Engl. J. Med.*, 305, 1489–1495.
27. Knowles, M., Gatzy, J. and Boucher, R. (1983) *J. Clin. Invest.*, 71, 1410–1417.
28. Li, M., McCann, J. D., Liedtke, C. M., Nairn, A. C., Greengard, P. and Welsh, M. J. (1988) *Nature*, 331, 358–360.
29. Mansour, S. L., Grodzicker, T. and Tjian, R. (1986) *Mol. Cell. Biol.*, 6, 2684–2694.
30. Mornex, J-F. Chytil-Weir, A., Martinet, Y., Courtney, M., LeCocq, J-P. and Crystal, R. G. (1986) *J. Clin. Invest.*, 77, 1952–1961.
31. Rich, D. P., Anderson, M. P., Gregory, R. J., Cheng, S. H., Paul, S., Jefferson, D. M., McCann, J. D., Klinger, K. W., Smith, A. E. and Welsh, M. J. (1990) *Nature*, 347, 358–363.
32. Riordan, J. R., Rommens, J. M., Kerem, B-S., Alon, N., Rozmahel, R., Grzelczak, Z., Zielenski, J., Lok, S., Plavsic, N., Chou, J-L., Drumm, M. L., Iannuzzi, M. C., Collins, F. S. and Tsui, L-C. (1989) *Science*, 245, 1066–1073.
33. Rommens, J. M., Iannuzzi, M. C., Kerem, B-S., Drumm, M. L., Melmer, G., Dean, M., Rozmahel, R., Cole, J. L., Kennedy, D., Hlidaka, N., Zsiga, M., Buchwald, M., Riordan, J. R., Tsui, L-C. and Collins, F. S. (1989) *Science*, 245, 1059–1064.
34. Rosenfeld, M. R., Siegfried, W., Yoshimura, K., Yoneyama, K., Fukayama, M., Stier, L. E., Paatkk6, P. K., Gilardi, P., Stratford-Perricaudet, L. D., Perricaudet, M., Jallet, S., Pavirani, A., LeCocq, J-P. and Crystal, R. G. (1991a) *Science* 252, 431–434.
35. Rosenfeld, M. R., Yoshimura, K., Stier, L. E., Trapnell, B. C., Stratford-Perricaudet, L. D., Perricaudet, M., Dalemans, W., Jallat, S., Mercenier, A., Pavirani, A., LeCocq, J-P. Guggino, W. B. and Crystal, R. G. (1991b) *Clin. Res.*, 39, 311A.
36. Roth, M. J., Tanese, N. and Goff, S. P. (1985) *J. Biol. Chem.*, 260, 9326–9335.
37. Saiki, R. K., Gelfand, D. H., Stoffel, S., Scharf, S. J., Higuchi, R., Horn, G. T., Mullis, K. B. and Erlich, H. A. (1988) *Science*, 239, 487–491.
38. Schoumacher, R. A., Ram, J., Iannuzzi, M. C., Bradbury, N. A., Wallace, R. W., Hon, C. T., Kelly, D. R., Schmid, S. M., Gelder, F. B., Rado, T. A. and Frizzell, R. A. (1990) *Proc. Natl. Acad. Sci. USA*, 87, 4012–4016.
39. Straus, S. E. (1984) In Ginsberg, H. S. (ed.), *The Adenoviruses*. Plenum Press, New York and London, pp. 451–496.
40. Thimmappaya, B., Weinberger, C., Schneider, R. J. and Shenk, T. (1982) *Cell*, 31, 543–551.
41. Trapnell, B. C., Zeitlin, P. L., Chu, C-S., Yoshimura, K., Nakamura, H., Guggino, W. B., Bargon, J., Banks, T., Dalemans, W., Pavirani, A., LeCocq, J-P. and Crystal, R. G. (1991a), *J. Biol. Chem.* 266, 10319–10323.
42. Trapnell, B. C., Chu, C-S., Paakko, P. K., Banks, T., Yoshimura, K., Ferans, V. J., Chernick, M. S. and Crystal, R. G. (1991b) *Proc. Natl. Acad. Sci. USA*, 88, 6565–6569.
43. Tso, J. Y., Sun, X-H., Kao, T-h., Reece, K. S. and Wu, R. (1985) *Nucl. Acids Res.*, 13, 2485–2502.
45. Weibel, E. R. (1991) In Crystal, R. G. and West, J. B. (eds.) *The Lung: Scientific Foundations*. Raven Press, Ltd., New York, 711–720.
46. Yoshimura, K., Nakamura, H., Trapnell, B. C., Dalemans, W., Pavirani, A., LeCocq, J-P. and Crystal, R. G. (1991) *J. Biol. Chem.*, 266, 9140–9144.
47. Zeitlin, P. L., Lu,L., Rhim, J., Cutting, G., Stetten, G., Kieffer, K. A., Craig, R. and Guggino, W. B. (1991) *Am. J. Respir. Cell. Mol. Biol.*, 4, 313–319.
48. Levrero M. et al. (1991) *Gene* 101 pp 195–202.
49. Gilardi et al., 1990, *FEBS Letters* 267 pp 60–62.

We claim:

1. A replication deficient recombinant adenovirus vector, the genome of which contains an expression cassette comprising a DNA molecule encoding the human CFTR protein operably associated with a promoter element that directs the expression of the CFTR protein, wherein the adenovirus vector comprises a deletion of the E1a, E1b, E3 regions.

2. The vector according to claim 1, wherein the DNA molecule is a cDNA that encodes normal human CFTR.

3. The vector according to claim 1 wherein the adenovirus is a type 5 adenovirus.

4. The vector according to claim 1 wherein the adenovirus is a type 5 adenovirus and wherein the deletion in the E1a and E1b regions has been replaced by the expression cassette.

5. The vector according to claim 1 wherein in the expression cassette the DNA molecule encoding the CFTR protein is under the control of a constitutive promoter.

6. The vector according to claim 5, where the promoter is the Ad 2 major late promoter.

7. The vector according to claim 1 wherein in the expression cassette the DNA fragment coding for the human CFTR is under the control of the endogenous human CFTR promoter or a mutated human CFTR promoter that is a functional equivalent of the human CFTR promoter.

8. The vector according to claim 1 wherein the CFTR expression cassette comprises successively from 5' to 3'

1) the ITR, the origin of replication, the encapsidation signal and the E1a enhancer of Ad5;

2) the major late promoter, and the Tripartite leader sequence of Ad2;

3) the DNA fragment coding for the human CFTR gene, and 4) the SV40 polyadenylation signal.

9. A replication defective adenovirus comprising a deletion in the E1a, E1b, and E3 regions and further comprising a transgene inserted in the E1 region, said transgene encoding a protein of interest operatively linked to a promoter heterologous to the transgene.

10. The replication defective adenovirus of claim 9 in which the heterologous promoter is Ad2 major late promoter.

11. A replication defective adenovirus comprising a deletion in the E1a, E1b, and E3 regions and further comprising a transgene encoding a non-selectable protein product operatively linked to a promoter heterologous to the transgene.

12. The replication defective adenovirus of claim 11 in which the heterologous promoter is Ad2 major late promoter.

13. A replication defective adenovirus comprising a deletion in the E1a, E1b, and E3 regions and further comprising a transgene encoding a mammalian protein operatively linked to a promoter heterologous to the transgene.

14. The replication defective adenovirus of claim 13 in which the heterologous promoter is Ad2 major late promoter.

15. A replication defective non-transforming adenovirus comprising a deletion in the E1a, E1b, and E3 regions and further comprising a DNA sequence encoding a protein of interest operatively linked to a promoter.

* * * * *

SEQUENCE LISTING (1) GENERAL INFORMATION:

(iii) NUMBER OF SEQUENCES: 6

(2) INFORMATION FOR SEQ ID NO:1:

-continued (i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:1:

AGCTGTTGGG GCTCGCGGTT GAGG                                          24

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:2:

CATCAAATTT GTTCAGGTTG TTGG                                          24

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:3:

AGTGGAGTGA TCAAGAAATA TGG                                           23

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:4:

GTAACCATTA TAAGCTGCAA TAAAC                                         25

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:5:

AATGCATCCT GCACCACCAA CTGC                                          24

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single

```
            (D) TOPOLOGY: unknown (ii) MOLECULE TYPE: DNA (xi) SEQUENCE DESCRIPTION: SEQ ID NO:6:

GGAGGCCATG TAGGCCATGA GGTC                                           24
```